(12) United States Patent
Wang et al.

(10) Patent No.: US 10,617,668 B2
(45) Date of Patent: Apr. 14, 2020

(54) PHARMACEUTICAL FORMULATIONS

(71) Applicant: Janssen Pharmaceutica NV, Beerse (BE)

(72) Inventors: Wenhua Wang, Newtown, PA (US); Todd Outwin, Chalfont, PA (US); Thomas C. Joseph, Oakford, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/400,005

(22) Filed: Jan. 6, 2017

(65) Prior Publication Data

US 2017/0112806 A1    Apr. 27, 2017

Related U.S. Application Data

(63) Continuation of application No. 14/486,014, filed on Sep. 15, 2014, now abandoned, which is a continuation of application No. 13/968,496, filed on Aug. 16, 2013, now abandoned, which is a continuation of application No. 13/105,008, filed on May 11, 2011, now abandoned.

(60) Provisional application No. 61/333,495, filed on May 11, 2010.

(51) Int. Cl.
| | | |
|---|---|---|
| *A61K 31/381* | (2006.01) | |
| *A61K 9/20* | (2006.01) | |
| *A61K 9/28* | (2006.01) | |
| *A61K 31/7042* | (2006.01) | |
| *A61K 31/7004* | (2006.01) | |
| *A61K 47/26* | (2006.01) | |
| *A61K 47/38* | (2006.01) | |
| *C07D 409/10* | (2006.01) | |

(52) U.S. Cl.
CPC .......... *A61K 31/381* (2013.01); *A61K 9/2013* (2013.01); *A61K 9/2018* (2013.01); *A61K 9/2054* (2013.01); *A61K 9/2866* (2013.01); *A61K 31/7004* (2013.01); *A61K 31/7042* (2013.01); *A61K 47/26* (2013.01); *A61K 47/38* (2013.01); *C07D 409/10* (2013.01)

(58) Field of Classification Search
CPC .. A61K 9/2054; A61K 9/2018; A61K 9/2013; A61K 31/381
USPC ......................................................... 514/23
See application file for complete search history.

(56) References Cited

U.S. PATENT DOCUMENTS

| | | |
|---|---|---|
| 2,799,241 A | 7/1949 | Wurster |
| 4,160,861 A | 7/1979 | Cole et al. |
| 4,584,369 A | 4/1986 | Klein et al. |
| 5,149,838 A | 9/1992 | Humphrey et al. |
| 5,292,461 A | 3/1994 | Juch et al. |
| 5,401,435 A | 3/1995 | Burzio et al. |
| 5,424,406 A | 6/1995 | Tsujihara et al. |
| 5,610,294 A | 3/1997 | Lam et al. |
| 5,731,292 A | 3/1998 | Tsujihara et al. |
| 5,767,094 A | 6/1998 | Tsujihara et al. |
| 5,780,483 A | 7/1998 | Widdowson et al. |
| 5,830,873 A | 11/1998 | Tsujihara et al. |
| 5,861,385 A | 1/1999 | Angerbauer et al. |
| 5,945,533 A | 8/1999 | Kometani et al. |
| 6,048,842 A | 4/2000 | Tsujihara et al. |
| 6,069,238 A | 5/2000 | Hitchcock et al. |
| 6,153,632 A | 11/2000 | Rieveley |
| 6,277,833 B1 | 8/2001 | Angerbauer et al. |
| 6,297,363 B1 | 10/2001 | Kubo et al. |
| 6,414,126 B1 | 7/2002 | Ellsworth et al. |
| 6,420,513 B2 | 7/2002 | Minami |
| 6,448,415 B1 | 9/2002 | Lee et al. |
| 6,475,521 B1 | 11/2002 | Timmins et al. |
| 6,479,661 B1 | 11/2002 | Buchholz et al. |
| 6,515,117 B2 | 2/2003 | Ellsworth et al. |
| 6,562,791 B1 | 5/2003 | Maurya et al. |
| 6,617,313 B1 | 9/2003 | Maurya et al. |
| 6,627,611 B2 | 9/2003 | Tomiyama et al. |

(Continued)

FOREIGN PATENT DOCUMENTS

| | | |
|---|---|---|
| CA | 2494177 A1 | 2/2004 |
| CN | 101057835 A | 10/2007 |

(Continued)

OTHER PUBLICATIONS

Adachi et al., "T-1095, a Renal $Na^+$-Glucose Transporter Inhibitor, Improves Hyperglycemia in Streptozotocin-Induced Diabetic Rats.", Metabolism, Aug. 2000, pp. 990-995, vol. 49(8).

(Continued)

*Primary Examiner* — Yih-Horng Shiao

(57) ABSTRACT

The present invention relates to formulations including compounds of Formula (I),

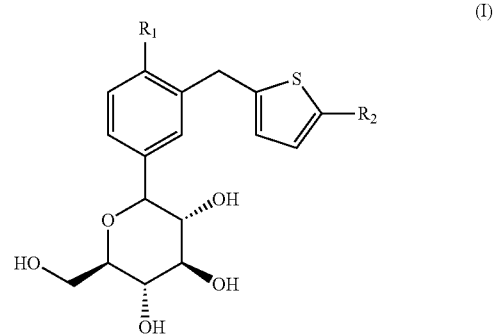

or prodrug, or a pharmaceutically acceptable salt thereof.

10 Claims, 2 Drawing Sheets

(56) References Cited

U.S. PATENT DOCUMENTS

| | | |
|---|---|---|
| 6,800,761 B1 | 10/2004 | Franc et al. |
| 7,008,959 B2 | 3/2006 | Franc et al. |
| 7,045,665 B2 | 5/2006 | Fujikura et al. |
| 7,074,826 B2 | 7/2006 | Wechter et al. |
| 7,084,123 B2 | 8/2006 | Fujikura et al. |
| 7,157,584 B2 | 1/2007 | Kuroita et al. |
| 7,202,350 B2 | 4/2007 | Imamura et al. |
| 7,271,153 B2 | 9/2007 | Nishimura et al. |
| 7,288,528 B2 | 10/2007 | Frick et al. |
| 7,294,618 B2 | 11/2007 | Fushimi et al. |
| 7,375,213 B2 | 5/2008 | Deshpande et al. |
| 7,417,032 B2 | 8/2008 | Eckhardt et al. |
| 7,511,022 B2 | 3/2009 | Beavers et al. |
| 7,566,699 B2 | 7/2009 | Fushimi et al. |
| 7,576,064 B2 | 8/2009 | Kikuchi et al. |
| 7,666,845 B2 | 2/2010 | Cook et al. |
| 7,932,379 B2 | 4/2011 | Deshpande et al. |
| 7,943,582 B2 | 5/2011 | Nomura et al. |
| 7,943,788 B2 | 5/2011 | Nomura et al. |
| 8,222,219 B2 | 7/2012 | Nomura et al. |
| 8,513,202 B2 | 8/2013 | Nomura et al. |
| 8,785,403 B2 | 7/2014 | Nomura et al. |
| 2001/0041674 A1 | 11/2001 | Tomiyama et al. |
| 2002/0032164 A1 | 3/2002 | Dale et al. |
| 2002/0052326 A1 | 5/2002 | Washburn |
| 2002/0111315 A1 | 8/2002 | Washburn et al. |
| 2002/0177602 A1 | 11/2002 | Piper et al. |
| 2002/0183345 A1 | 12/2002 | Piper et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0141023 A1 | 6/2006 | Trehan et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2007/0299033 A1 | 12/2007 | McMahon et al. |
| 2008/0004336 A1 | 1/2008 | Gougoutas et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2009/0143316 A1 | 6/2009 | Imamura et al. |
| 2009/0233874 A1 | 9/2009 | Abdel-Magid et al. |
| 2010/0063141 A1 | 3/2010 | Seed et al. |
| 2010/0099883 A1 | 4/2010 | Filliers et al. |
| 2011/0009347 A1 | 1/2011 | Liang et al. |
| 2011/0087017 A1 | 4/2011 | Farina et al. |
| 2011/0171159 A1 | 7/2011 | Berbernitz et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |
| 2012/0165410 A1* | 6/2012 | Dodd .................. A61K 9/145 514/569 |

FOREIGN PATENT DOCUMENTS

| | | |
|---|---|---|
| EP | 0355750 A1 | 2/1990 |
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1528066 A1 | 5/2005 |
| EP | 1845095 | 10/2007 |
| EP | 1956023 A1 | 3/2008 |
| GB | 2359554 | 8/2001 |
| JP | 59039889 A | 3/1984 |
| JP | 63-233975 A | 9/1988 |
| JP | 2007-23099 | 6/1989 |
| JP | H03-503280 | 7/1991 |
| JP | 4-253974 A | 9/1992 |
| JP | 06246354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-12686 A1 | 1/2003 |
| JP | 2003238417 A | 8/2003 |
| JP | 2003313168 A | 11/2003 |
| JP | 2008-280345 A | 11/2008 |
| WO | WO 1989/05639 A1 | 6/1989 |
| WO | WO 1993/09100 A1 | 5/1993 |
| WO | WO 1993/21178 A1 | 10/1993 |
| WO | WO 1994/14807 A1 | 7/1994 |
| WO | WO 1996/13258 A1 | 5/1996 |
| WO | WO 1997/17949 A1 | 5/1997 |
| WO | WO 1997/25033 A1 | 7/1997 |
| WO | WO 1998/42347 A1 | 10/1998 |
| WO | WO 1999/061026 A1 | 12/1999 |
| WO | WO 1999/065861 A1 | 12/1999 |
| WO | WO 1999/67236 A | 12/1999 |
| WO | WO 2000/27823 A1 | 5/2000 |
| WO | WO 2000/28989 A1 | 5/2000 |
| WO | WO 2000/74681 A1 | 12/2000 |
| WO | WO 2001/27128 | 4/2001 |
| WO | WO 2001/032157 A2 | 5/2001 |
| WO | WO 2001/032158 A2 | 5/2001 |
| WO | WO 2001/64669 A1 | 9/2001 |
| WO | WO 2001/68660 A1 | 9/2001 |
| WO | WO 2001/74834 A1 | 10/2001 |
| WO | WO 2001/74835 A1 | 10/2001 |
| WO | WO 2001/085167 A1 | 11/2001 |
| WO | WO 2002/026706 A2 | 4/2002 |
| WO | WO 2002/053573 A1 | 7/2002 |
| WO | WO 2002/068439 A1 | 9/2002 |
| WO | WO 2002/068440 A1 | 9/2002 |
| WO | WO 2002/070020 A2 | 9/2002 |
| WO | WO 2002/070020 A3 | 9/2002 |
| WO | WO 2002/083066 A2 | 10/2002 |
| WO | WO 2002/088157 A1 | 11/2002 |
| WO | WO 2002/094262 A1 | 11/2002 |
| WO | WO 2002/096357 A2 | 12/2002 |
| WO | WO 2003/000712 A1 | 1/2003 |
| WO | WO 2003/011880 A1 | 2/2003 |
| WO | WO 2003/020737 A1 | 3/2003 |
| WO | WO 2003/040121 A1 | 5/2003 |
| WO | WO 2003/043621 A1 | 5/2003 |
| WO | WO 2003/087104 A1 | 10/2003 |

(56) References Cited

FOREIGN PATENT DOCUMENTS

| | | |
|---|---|---|
| WO | WO 2003/099836 A1 | 12/2003 |
| WO | WO 2004/007517 A1 | 1/2004 |
| WO | WO 2004/013118 A1 | 2/2004 |
| WO | WO 2004/014931 A1 | 2/2004 |
| WO | WO 2004/019958 A1 | 3/2004 |
| WO | WO 2004/052902 A1 | 6/2004 |
| WO | WO 2004/052903 A1 | 6/2004 |
| WO | WO 2004/063209 A2 | 7/2004 |
| WO | WO 2004/063209 A3 | 7/2004 |
| WO | WO 2004/064806 A | 8/2004 |
| WO | WO 2004/076470 A2 | 9/2004 |
| WO | WO 2004/080990 A1 | 9/2004 |
| WO | WO 2004/087727 A1 | 10/2004 |
| WO | WO 2004/099230 A1 | 11/2004 |
| WO | WO 2004/113359 A1 | 12/2004 |
| WO | WO 2005/009539 A2 | 2/2005 |
| WO | WO 2005/009954 A2 | 2/2005 |
| WO | WO 2005/012326 A1 | 2/2005 |
| WO | WO 2005/058845 A2 | 6/2005 |
| WO | WO 2006/007448 A2 | 1/2006 |
| WO | WO 2006/010557 | 2/2006 |
| WO | WO 2006/080577 A1 | 8/2006 |
| WO | WO 2006/108842 A1 | 10/2006 |
| WO | WO 2007/025943 A2 | 3/2007 |
| WO | WO 2007/031548 A2 | 3/2007 |
| WO | WO 2007/087441 A2 | 8/2007 |
| WO | WO 2008/002824 A1 | 1/2008 |
| WO | WO 2008/013322 A1 | 1/2008 |
| WO | WO 2008/020011 A2 | 2/2008 |
| WO | WO 2008/034859 A1 | 3/2008 |
| WO | WO 2008/050987 A1 | 5/2008 |
| WO | WO 2008/055870 A1 | 5/2008 |
| WO | WO 2008/055940 A2 | 5/2008 |
| WO | WO 2008/069327 A1 | 6/2008 |
| WO | WO 2008/070609 A1 | 6/2008 |
| WO | WO 2008/113000 A1 | 9/2008 |
| WO | WO 2008/136392 A1 | 11/2008 |
| WO | WO 2009/022010 A1 | 2/2009 |
| WO | WO 2009/023537 | 2/2009 |
| WO | WO 2009/035969 A1 | 3/2009 |
| WO | WO 2009/091082 A1 | 7/2009 |
| WO | WO 2009/121945 A2 | 10/2009 |
| WO | WO 2009/125975 A2 | 10/2009 |
| WO | WO 2010/009243 A1 | 1/2010 |
| WO | WO 2010/022313 A2 | 2/2010 |
| WO | WO 2010/045656 A2 | 4/2010 |
| WO | WO 2010/092125 A1 | 8/2010 |
| WO | WO 2011/047113 A1 | 4/2011 |
| WO | WO 2011/048112 A1 | 4/2011 |
| WO | WO 2011/120923 A1 | 10/2011 |
| WO | WO 2012/006298 * | 1/2012 |

OTHER PUBLICATIONS

Ahmad et al., "Synthesis and Structure Determination of Some Oxadiazole-2-Thione and Triazole-3-Thione Galactosides.", *Nucleosides, Nucleotides & Nucleic Acids*, 2001, pp. 1671-1682, vol. 20(9).
Albertoni Borghese et al., "Inhibitors of sodium/glucose cotransport.", Drugs of the Future, Apr. 2009, pp. 297-305, vol. 34(4), Prous Science, XP007915342.
Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, pp. 1393-1403, vol. 47(10).
Appleton et al., "A Mild and Selective C-3 Reductive Alkylation of Indoles", Tetrahedron Letters, 1993, pp. 1529-1532, vol. 34(9).
Apsei et al., "General Entries to C-aryl glycosides. Formal synthesis of galtamycinone.", Tetrahedron Letters, 2003, pp. 1075-1077, vol. 44.
Arakawa et al., "Improved diabetic syndrome in C57BL/KsJ-db/db Mice by Oral Administration of the Na+-Glucose Cotransporter Inhibitor T-1095.", *British Journal of Pharmacology*, 2001, pp. 578-586, vol. 132.
Banker, Modern Pharmaceutics, Third Edition, Marcel Dekker, Inc., published 1996, p. 596.
Beck-Nielsen et al., "In Vivo Glucose Metabolism, Insulin Secretion and, Insulin Action in Europids with non-insulin-dependent Diabetes mellitus (NIDDM) and Their First-degree Relatives.", Diabetic Medicine, Sep. 1996, pp. S78-S84, vol. 13(9 Supp. 6).
Benhaddou et al., "Tetra-n-propylammonium tetra-oxoruthenate(VII): a reagent of choice for the oxidation of diversely protected glycopyranoses and glycofuranoses to lactones", Carbohydrate Research, 1994, pp. 243-250, vol. 260.
Bertolini et al., "A New Simple One-Pot Regioselective Preparation of Mixed Diesters of Carbonic Acid.", Journal of Organic Chemistry, 1998, pp. 6031-6034, vol. 63(17).
Blair et al., "Effect of Ring Fluorination on the Pharmacology of Hallucinogenic Tryptamines", J. Med. Chem., 2000, pp. 4701-4710, vol. 43.
Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, pp. 2664-2674, vol. 43(14).
Bookser, B.C., "2-Benzyloxymethyl-5-(tributylstannyptetrazole. A reagent for the preparation of 5-aryl-and 5-heteroaryl-1H-tetrazoles via the Stille reaction," Tetrahedron Letters, 2000, pp. 2805-2809, vol. 41.
Bouillon et al., "Synthesis of novel halopyridinylboronic acids and esters. Part 2: 2,4, or 5-Halopyridin-3-yl-boronic acids and esters," Tetrahedron, 2002, pp. 3323-3328, vol. 58.
Bouillon et al., "Synthesis of novel halopyridinylboronic acids and esters. Part 3: 2, or 3-Halopyridin-4-yl-boronic acids and esters," Tetrahedron, 2002, pp. 4369-4373, vol. 58.
Bouillon et al., "Synthesis of novel halopyridinylboronic acids and esters. Part 4: Halopyridin-2-yl-boronic acids and esters are stable, crystalline partners for classical Suzuki cross-coupling," Tetrahedron, 2003, pp. 10043-10049, vol. 59.
Braga et al., "Making crystals from crystals: a green route to crystal engineering and polymorphism.", Chem. Comm., 2005, pp. 3635-3645.
Brooks et al., "Boron Trichloride/Tetra-n-Butylammonium Iodide: A Mild, Selective Combination Reagent for the Cleavage of Primary Alkyl Aryl Ethers", J. Org. Chem., 1999, pp. 9719-9721, vol. 64.
CAS Reg. No. 487001-40-1, IPOrganisers, Entered STN Feb. 7, 2003, pp. 1-2.
Caumo et al., "Insulin Sensitivity from Meal Tolerance Tests in Normal Subjects: A Minimal Model Index.", J. of Clinical Endocrinology & Metabolism, 2000, pp. 4396-4402, vol. 85(11).
Cicchillo et al., "A convenient synthesis of glycosyl chlorides from sugar hemiacetals using triphosgene as the chlorine source," Carbohydrate Research, 2000, pp. 431-434, vol. 328.
Clayden et al., "Dearomatizing Cyclization of Arylsulfonylalkoxymethyl Lithiums: A Route to the Podophyllotoxin Skeleton," Organic Letters, 2003, pp. 831-834, vol. 5(6).
Comins et al., "Synthesis of 3-Substituted Indoles Via N-Acylindolium Ions", Tetrahedron Letters, 1986, pp. 1869-1872, vol. 27(17).
Cottet et al., "Recommendable Routes to Trifluoromethyl-Substituted Pyridine—and Quinolinecarboxylic Acids," Eur. J. Org. Chem., 2003, pp. 1559-1568.
Czernecki et al., "C-Glycosides. 7. Stereospecific C-Glycosylation of Aromatic and Heterocyclic Rings", J. Org. Chem., 1989, pp. 610-612, vol. 54.
De Las Heras et al., "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979,pp. 496-501, vol. 22(5).
Deeg et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, pp. 2458-2464, vol. 30(10).
Deetjen et al., "Renal Handling of D-Glucose and Other Sugars", Textbook of Nephrology, 3rd Edition, 1995, pp. 90-94. vol. 1.
Devivar et al., "Benzimidazole Ribonucleosides: Design, Synthesis, and Antiviral Activity of Certain 2-(Alkylthio)- and 2-(Benzylthio)-

(56) References Cited

OTHER PUBLICATIONS 5,6-dichloro-1-(.beta.-D-ribofuranosyl)benzimidazolesl.", J. Med. Chem., 1994, pp. 2942-2949, vol. 37.
Dewynter et al., "Synthesis of Pseudomucleosides containing Chiral Sulfahydantoins as Aglycone (II)", Tetrahedron, 1996, pp. 993-1004, vol. 52(3).
Dillard et al., "Indole Inhibitors of Human Nonpancreatic Secretory Phospholipase A2. 1. Indole-3-acetamides", J. Med. Chem., 1996, pp. 5119-5136, vol. 39.
Dinneen, S.F., "The Postprandial State: Mechanisms of Glucose Intolerance.", Diabetic Medicine, Aug. 1997, pp. S19-S24, vol. 14, Issue S3.
Dondoni et al., "Stereoselective synthesis of C-glycosylphosphonates from their ketols. Reconsideration of an abandoned route", Tetrahedron: Asymmetry, 2000, pp. 305-317, vol. 11.
Dondoni et al., "Thiazole-Based Synthesis of Formyl C-Glycosides", J. Org. Chem., 1994, pp. 6404-6412, vol. 59.
Dudash et al., "Glycosylated dihydrochalcones as potent and selective sodium glucose co-transporter 2 (SGLT2) inhibitors," Bioorganic & Medicinal Chemistry Letters, 2004, pp. 5121-2125, vol. 14.
Dunn et al., "Analgetic and antiinflammatory 7-Aroylbenzofuran-5-ylacetic acids and 7-Aroylbenzothiophene-5-ylacetic Acids.", Journal of Med. Chem., 1986, pp. 2326-2329, vol. 29(1).
Eid et al., "Reaction of Some 1,2,4-Triazines with Acetobromoglucose", Arch. Pharm (Weinheim), 1990, pp. 243-245, vol. 323.
Ellsworth et al., "Aglycone exploration of C-arylglucoside inhibitors of renal sodium-dependent glucose transporter SGLT2," Bioorganic & Medicinal Chemistry Letters, 2008, pp. 4770-4773, vol. 18.
Ellsworth et al., "C-Arylglucoside synthesis: triisopropylsilane as a selective reagent for the reduction of an anomeric C-phenyl ketal," Tetrahedron: Asymmetry, 2003, pp. 3243-3247, vol. 14.
Emancipator, K., "Laboratory diagnosis and monitoring of diabetes mellitus.", Am J Clin Pathol., Nov. 1999, pp. 65-674, vol. 112(5).
Frahn et al., "Functionalized AB-Type Monomers for Suzuki Polycondensation," Synthesis, Nov. 1997, pp. 1301-1304.
Fresneda et al., "Synthesis of the indole alkaloids meridianins from the tunicate Aplidium meridianum" Tetrahedron, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.
Ganesh et al., "Synthesis and biological evaluation of fluorescently labeled epothilone analogs for tubulin binding studies," Tetrahedron, 2003, pp. 9979-9984.
Gershell, L., "Type 2 diabetes market", Nature Reviews Drug Discovery, May 2005, pp. 367-368, vol. 4.
Gohier et al., "Ortho-Metalation of Unprotected 3-Bromo and 3-Chlorobenzoic Acids with Hindered Lithium Dialkylamides," J. Org. Chem., 2003, pp. 2030-2033, vol. 68.
Goldberg R.B., "Prevention of Type 2 Diabetes.", Medical Clinics of North America, Jul. 1998, pp. 805-821, vol. 82(4).
Gong, H., et al., "Diasteroselective Ni-Catalyzed negishi Cross Coupling Approach to Saturated, Fully Oxygenated C-Alkyl and C-Aryl Glycosides.", Journal of The American Chemical Society, Sep. 10, 2008, pp. 12177-12183, vol. 130(36), XP002612364.
Goodman & Gilman's the Pharmacological Basis of Therapeutics, 10th Edition, McGraw-Hill Medical Publishing Division, 2001, pp. 54-57.
Greene et al., "Protective Groups in Organic Synthesis.", 3rd Edition, 1999, pp. 116-121.
Greene et al., "Protective Groups in Organic Synthesis.", 3rd Edition, 1999, pp. 170.
Gronowitz et al., "Some Substitution Reactions of 1-(2-Thienyl)pyrazole and 1-(3'-Thienyl)pyrazole," Chemica Scripta., 1979, pp. 157-161, vol. 13.
Groop et al., "Characterization of the Prediabetic State.", American Journal of Hypertension, Sep. 1997, pp. 172S-180S, vol. 10(9Part2).
Gros et al., "Efficient and Regioselective Access to Bis-heterocycles via Palladium-Catalysed Coupling of Organostannanes and Organozincates Derived from C-6 Lithiated 2 Methoxypyridine," Synthesis, 1999, pp. 754-756, No. 5.
Haffner S.M., "Impaired Glucose Tolerance, Insulin Resistance and Cardiovascular Disease.", Diabetic Medicine, Aug. 1997, pp. S12-S18, vol. 14.
Haffner S.M., "The Prediabetic Problem: Development of Non-Insulin-Dependent Diabetes Mellitus and Related Abnormalities.", Journal of Diabetes and Its Complications, Mar.-Apr. 1997, pp. 69-76, vol. 11(2).
Han et al., "Dapagliflozin, a Selective SGLT2 Inhibitor, Improves Glucose Homeostasis in Normal and Diabetic Rats", Diabetes, Jun. 2008, pp. 1723-1729, vol. 57, New York.
Handlon, A. L., "Sodium glucose co-transporter 2 (SGLT2) inhibitors as potential antidiabetic agents," Expert Opin. Ther. Patents, 2005, pp. 1531-1540, vol. 15(11).
Hixon et al., "Sizing Materials by Crushing and Grinding.", Chemical Engineer, Nov. 1990, pp. 94-103.
Hofslokken et al., "Convenient Method for the ortho-Formylation of Phenols.", Acta Chemica Scandinavica, 1999, pp. 258-262, vol. 53.
Hongu et al., "Na$^+$-Glucose Cotransporter Inhibitors as Antidiabetic Agents. II.[1]) Synthesis and Structure—Activity Relationships of 4'-Dehydroxyphlorizin Derivatives." Chem. Pharm. Bull., 1998, pp. 22-33, vol. 46(1).
Horton et al., "Synthetic Routes to Higher-Carbon Sugars. Reaction of Lactones with 2-Lithio-1,3-Dithiane", Carbohydrate Research, 1981, pp. 27-41, vol. 94.
Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, pp. 43-48, vol. 53(1).
Huang-Minlon, "Reduction of Steroid Ketones and other Carbonyl Compounds by Modified Wolff-Kishner Method", J. Am. Chem. Soc., Oct. 1949, pp. 3301-3303, vol. 71.
Ibrahim et al., "Facile Approach for the Selective Glycodisation of Cyclic Asymmetric Amides and Thioamides", Carbohydrate Letters, 1996, pp. 425-432, vol. 1.
Ibrahim et al., "Selective Synthesis and Structure of 2-N- and 3-S-Glucosyl-1,2,4-Triazoles of Potential Biological Interest", Carbohydrate Letters, 1999, pp. 331-338, vol. 3(5).
Idris et al., "Sodium-glucose co-transporter-2 inhibitors: an emerging new class of oral antidiabetic drug.", Diabetes, Obesity and Metabolism, 2009, pp. 79-88, vol. 11(2), GB, XP007915350.
Isaji, M., "Sodium-glucose cotransporter inhibitor for diabetes," Current Opinion in Investigational Drugs, 2007, pp. 285-292, vol. 8(4).
Jain et al., "Polymorphism in Pharmacy.", Indian Drugs, 1986, pp. 315-329, vol. 23(6).
Kaelin et al., "General Strategies for the Synthesis of the Major Classes of C-aryl Glycosides.", J. Am. Chem. Soc., 2001, pp. 6937-6938, vol. 123.
Kahn et al., "Normalization of Blood Glucose in Diabetic Rats with Phlorizin Treatment Reverses Insulin-resistant Glucose Transport in Adipose Cells without Restoring Glucose Transporter Gene Expression.", Journal of Clinical Investigation, 1991, pp. 561-570, vol. 87.
Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, pp. 397-404, vol. 93.
Kasahara et al., "A missense mutation in the Na+/glucose cotransporter gene SGLT1 in a patient with congenital glucose-galactose malabsorption: normal trafficking but inactivation of the mutant protein," Biochimica et Biophysics Acta, 2001, pp. 141-147, vol. 1536.
Katz et al., "Quantitative Insulin Sensitivity Check Index: A Simple, Accurate Method for Assessing Insulin Sensitivity in Humans.", J. of Clin. Endocrinology & Metabolism, 2000, pp. 2040-2410, vol. 85(7).
Ketcha et al., "Synthesis of Alyl-Substituted N-Protected Indoles via Acylation and Reductive Deoxygenation1" J. Org. Chem., 1989, pp. 4350-4356, vol. 54.
Khan et al, "Reactions of Phenyl-Substituted Heterocyclic Compounds—II. Nitrations and Brominations of 1-Phenylpyrazole Derivatives," Canadian Journal of Chemistry, 1963, pp. 1540-1547, vol. 41.

(56) References Cited

OTHER PUBLICATIONS

Kitagawa, K., et al., "Halogen—Magnesium Exchange via Trialkylmagnesates for the Preparation of Aryl- and Alkenylmagnesium Reagents", Angew. Chem. Int. Ed., 2000, pp. 2481-2493, vol. 39(14).
Klapars et al., "Copper-Catalyzed Halogen Exchange in Aryl Halides: An Aromatic Finkelstein Reaction", J. Am. Chem. Soc., 2002, pp. 14844-14845, vol. 124(50).
Knochel, P., et al., Organic Reactions, vol. 58, Chapter 2: Preparation and Application of Functionalized Organozinc Compounds, 2001, pp. 417-490, Edited by L. E. Overman, et al., John Wiley &Sons, Inc., Publishers.
Lee et al., "Recent Advances in Aryl C-Glycoside Synthesis.", Current Topics in Medicinal Chemistry, 2005, pp. 1333-1350, vol. 5.
Lee et al., "Synthesis and in Vitro Activity of Novel Isoxazolyl Tetrahydropyridinyl Oxazolidinone Antibacterial Agents," Bioorganic & Medicinal Chemistry Letters, 2003, pp. 4117-4120, vol. 13.
Lieberman et al., "Pharmaceutical Dosage Forms.", Second Edition, 1990, Marcel Dekker Inc., pp. 462-472, vol. 2.
Lin et al., "Syntheses of Guanidinoglycosides with the Inventive use of Mitsunobu Conditions and 1, 8-Diazabicyclo[5.4.0]undec-7-ene.", Synthesis, 2003, pp. 255-261, No. 2.
Link et al., "A method for preparing C-glycosides related to phlorizin" Tetrahedron Letters, 2000, pp. 9213-9217, vol. 41.
Lipscombe et al., "Trends in diabetes prevalence, incidence, and mortality in Ontario, Canada 1995-2005: a population-based study", Lancet, 2007, vol. 369, pp. 750-756.
Maatooq et al., "C-p-Hydroxybenzoylglycoflavones From Citrullus Colocynthis.", *Phytochemistry*, Jan. 1997, pp. 187-190, vol. 44(1).
MacKenzie et al., "Biophysical Characteristics of the Pig Kidney Na+/Glucose Cotransporter SGLT2 Reveal a Common Mechanism for SGLT1 and SGLT2", J. Biol. Chem., 1996, vol. 271, pp. 32678-32683, No. 5.
Manis et al., "Metabolism of 4,4'-Methylenebis(2-chloroaniline) by Canine Liver and Kidney Slices.", Drug Metabolism and Disposition, 1986, pp. 166-174, vol. 14(2).
Marsenic, O. MD, "Glucose Control by the Kidney: An Emerging Target in Diabetes.", Am. J. of Kidney Diseases, May 2009, pp. 875-883, vol. 53(5).
Martin, S. F., "Unified Strategy for the Synthesis of C-aryl glycosides*.", Pure Appl. Chem., 2003, pp. 63-70, vol. 75(1).
Matsuda et al., "Insulin Sensitivity Indices Obtained From Oral Glucose Tolerance Testing: Comparison with the euglycemic insulin clamp," Diabetes Care, Sep. 1999, pp. 1462-1470, vol. 22(9).
Matthews et al., "Homeostasis model assessment: insulin resistance and—cell function from fasting plasma glucose and insulin concentrations in man," Diabetolgia, 1985, pp. 412-419, vol. 28.
Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).
Meng et al., "Discovery of Dapagliflozin: a Potent, Selective Renal Sodium-Dependent Glucose Cotransporter2 (SGLT2) Inhibitor for the Treatment of Type 2 Diabetes", J. Med. Chem., 2008, pp. 1145-1149, vol. 51(5).
Messaoudi et al, "Synthesis and biological evaluation of oxindoles and benzimidazolinones derivatives," European Journal of Medicinal Chemistry, 2004,pp. 453-458.
Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.
Miyaura et al., "Palladium-Catalyzed Cross-Coupling Reactions of Organoboron Compounds.", Chem. Rev., 1995, pp. 2457-2583, vol. 95(7).
Mongin, F., et al., "Deprotonation of furans using lithium magnesates", Tetrahedron Lett., 2005, pp. 7989-7992, vol. 46.

Nishimura et al, "Tissue-specific mRNA Expression Profiles of Human ATP-binding Cassette and Solute Carrier Transporter Superfamilies," Drug Metab. Pharmacokinet., 2005, pp. 452-477, vol. 20(6).
Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.
Nomura, S., "Renal Sodium-Dependent Glucose Cotransporter2 (SGLT2) Inhibitors for New Anti-Diabetic Agent," Current Topics in Medicinal Chemistry, 2010, pp. 411-418, vol. 10(4).
Ohsumi et al. "Pyrazole-O-Glucosides as Novel Na+-Glucose Cotransporter (SGLT) Inhibitors" Bioorganic & Medicinal Chemistry Letters, 2003, pp. 2269-2272, vol. 13.
Oku et al., "T-1095, an Inhibitor of Renal Na+-Glucose Cotransporters, May Provide a Novel Approach to Treating Diabetes", Diabetes, Sep. 1999, pp. 1794-1800, vol. 48.
Orjales et al. "New 2-Piperazinylbenzimidazole Derivatives as 5-HT-3 Antagonists. Synthesis and Pharmacological Evaluation," J. Med. Chem., 1997, pp. 586-593, vol. 40.
Parker et al., "Reductive Aromatization of Quinols: Synthesis of the C-Arylglycoside Nucleus of the Paulacandins and Chaetiacandin," Organic Letters, 2000, pp. 497-499, vol. 2(4).
Parrott, E.L., "Milling of pharmaceutical solids.", Journal of Pharmaceutical Sciences, Jun. 1974, pp. 813-829, vol. 63(6).
Patani et al., "Bioisosterism: A Rational Approach in Drug Design", Chem. Rev., American Chemical Society, 1996, pp. 3147-3176, vol. 96.
Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).
Perry's Chemical Engineers Handbook, Sixth Edition, 1984, pp. 21-13 to 21-19.
Pharmaceutical Sciences, Remington, 17th Ed., pp. 1585-1594 (1985).
Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.
Ramlo-Halsted B.A. & Edelman S.V., "The Natural History of Type 2 Diabetes Mellitus: Implications for Clinical Practice.", Primary Care, Dec. 1999, pp. 771-789, vol. 26(4).
Raynaud et al., "Revised Concept for the Estimation of Insulin Sensitivity From a Single Sample.", Diabetes Care, Jun. 1999, pp. 1003-1004, vol. 22(6).
Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.
Rosetti et al., "Correction of Hyperglycemia with Phlorizin Normalizes Tissue Sensitivity to Insulin in diabetic rats.", *Journal of Clinical Investigation*, 1987, pp. 1510-1515, vol. 79.
Rosetti et al., "Effect of Chronic Hyperglycemia on In Vivo Insulin Secretion in Partially Pancreatectomized Rats.", *Journal of Clinical Investigation*, 1987, pp. 1037-1044, vol. 80.
Rosetti et al., "Glucose Toxicity."; *Diabetes Care*, 1990, pp. 610-630, vol. 13.
Schmidt et al., "Synthese von Pyrazol-, Pyrazolo[3,4-d]pyrimidin- und 1H-1,2,4-Triazolgluconucleosiden aus Glucosehydrazonen," Liebigs Ann. Chem., 1981, pp. 2309-2317.
Schultheiss et al., "Pharmaceutical Cocrystals and Their Physicochemical Properties.", Crystal Growth and Design, Jun. 3, 2009, pp. 2950-2967, vol. 9(6), XP55011939.
Shan et al., "The role of cocrystals in pharmaceutical science.", Drug Discovery Today, May 1, 2008, pp. 440-446, vol. 13(9-10), Elsevier, Rahway, NJ,US, XP022649919.
Silverman, R. B., "The Organic Chemistry of Drug Design and Drug Action," Academic Press,1992, pp. 19-23.
Somei et al., "The First and Simple Total Synthesis of Cappariloside AI," Heterocycles, 2000, pp. 1573-1578, vol. 53(7).

(56) References Cited

OTHER PUBLICATIONS

Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.
Stoner et al., "Benzylation via Tandem Grignard Reaction—Lodotrimethylsilane (TMSI) Mediated.Reduction," Tetrahedron, 1995, pp. 11043-11062, vol. 51(41).
Stumvoll et al., "Use of the Oral Glucose Tolerance Test to Assess Insulin Release and Insulin Sensitivity.", Diabetes Care, Mar. 2000, pp. 295-301, vol. 23(3).
Tanaka et al. "Solid-Phase Synthesis of—Mono-Substituted Ketones and an Application to the Synthesis of a Library of Phlorizin Derivatives", Synlett, 2002, pp. 1427-1430, No. 9.
Thornber, C.T., "Isosterism and Molecular Modification in Drug Design.", Chem. Society Review, 1979, pp. 563-580, vol. 8.
Tilak et al, "Carcinogenesis by Thiophene Isosters of Polycyclic Hydrocarbons," Tetrahedron, 1960, pp. 76-95, vol. 9.
Tsujihara et al., "Na+ Glucose Cotransporter (SGLT) Inhibitors as Antidiabetic Agents. 4. Synthesis and Pharmacological Properties of 4'-Dehydroxyphlorizin Derivatives Substituted on the B Ring.", *Journal of Medicinal Chemistry*, 1999, pp. 5311-5324, vol. 42.
Tsujihara et al., Bio Clinica, 1998, pp. 324-328, vol. 13(4), English language Abstract.
Turk et al., "Glucose/galactose malabsorption caused by a defect in the Na+/glucose cotransporter," Nature, Mar. 1991, pp. 354-356, vol. 350.
Ueta et al., "Long-term treatment with the Na+-glucose contransporter inhibitor T1095 causes sustained improvement in hyperglycemia and prevents diabetic neuropathy in Goto-Kakizaki Rats.", *Life Sci.*, 2005, pp. 2655-2668, vol. 76(23).
Unger et al., "Hyperglycemia as an inducer as well as a consequence of impaired islet cell function and insulin resistance: implications for the management of diabetes.", *Diabetologia*, 1985, pp. 119-121, vol. 28.
Vippagunta et al., "Crystalline Solids" Advanced Drug Delivery Reviews, 2001, pp. 3-26, vol. 48.
Vishweshwar et al., "Pharmaceutical co-crystals.", Journal of Pharmaceutical Sciences, Mar. 1, 2006, pp. 499-516, vol. 95(3), American Pharmaceutical Association, Washington, US.
Wallace et al., "Use and Abuse of Homa Modeling.", Diabetes Care, Jun. 2004, pp. 1487-1495, vol. 27(6).
Wang et al, "Selective monolithiation of 2,5-dibromopyridine with butyllithium," Tetrahedron Letters, 2000, pp. 4335-4338, vol. 41.
Wareham et al., "Is There Really an epidemic of diabetes?", Diabetologia, 2005, pp. 1454-1455, vol. 48.
Washburn, W. N., "Evolution of sodium glucose co-transporter 2 inhibitors as anti-diabetic agents," Expert Opin. Ther. Patents, 2009, pp. 1485-1499, vol. 19(11).
Watanabe et al., "Cyclopentyl Methyl Ether as a New and Alternative Process Solvent.", Organic Process Research and Development, 2007, pp. 251-258, vol. 11.
Wild et al., "Global Prevalence of Diabetes: Estimates for the year 2000 and projections for 2030," Diabetes Care, May 2004, pp. 1047-1053, vol. 27(5).
Wolff, M. E., vol. 1: Principles and Practice, Burger's Medicinal Chemistry and Drug Discovery, 5th Edition, 1995, pp. 975-977.
Wright, E.M., "Renal Na+-glucose cotransporters," Am J Physiol Renal Physiol, 2001, pp. F10-F18, vol. 280.
Wurster D.E., "Air-suspension Technique of Coating Drug Particles* A Preliminary Report.", Journal of the American Pharmaceutical Association, Aug. 1959, pp. 451-454, vol. 48(8).
Wurster, D.E., "Preparation of compressed tablet granulations by the air-suspension technique II.", Journal of the American Pharmaceutical Association, 1960, pp. 82-84, vol. 49(2).
Yang et al., "Convergent C-Glycolipid Synthesis via the Ramberg-Backlund Reaction: Active Antiproliferative Glycolipids", Org. Lett. 1999, pp. 2149-2151, vol. 1913.

Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," J. Med. Chem., 2000, pp. 2929-2937, vol. 43.
Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.
Zhdanov, Y. et al., "Application of organozinc compounds in the synthesis of carbon-carbon derivatives of sugars", Database CA (online), Chemical Abstracts Service, 2001, Columbus, Ohio, USA, XP002612365.
Zhou, F.Y., "The Synthesis and Characterization of 1-Benzyl-3-N-(Beta-D-glucosie-1-yl)-4-fluorouracil", Hecheng Huaxue, 2001, pp. 272-274, vol. 9(3).
Jianqun, et al., "Recent advances in palladium catalysts for aryl chlorides coupling reaction", Industrial Catalysis, Jul. 31, 2005, pp. 29-44, vol. 13(7).
Zhiyin, et al., "Cross-coupling reaction of Grignard reagent with thiophenyl halides by using nickel phosphine as catalyst and the synthesis of α-terthienyl", Huaxue Shiji, Dec. 31, 1995, pp. 289-290, vol. 17(5).
Clinical Trial NTC00707954, ClinicalTrials.gov/archive/NTC00707954/ 2008_06_30, View of Trial on Jun. 30, 2008.
Clinical Trial NTC00642278, Clinical Trials.gov/archive/ NTC00642278, View of Trial on Jun. 20, 2009.
Clinical Trial, "An Efficacy, Safety, and Tolerability Study of Canagliflozin (JNJ-28431754) in Patients With Type 2 Diabetes.", Clinical Trial NTC00642278, accessed Mar. 20, 2015.
Asahara et al. *Handbook of Solvents*, K.K. Kodansah., Sep. 1, 1985, Sixth Printing, pp. 47-51, Tokyo, JP.
Byrn et al., "Pharmaceutical Solids: A Strategic Approach to Regulatory Considerations.", Pharml. Res., 1995, pp. 945-954, vol. 12(7).
Kozikowski et al., Organometallics in Organic Synthesis. Applications of a New Diorganozinc Reaction to the Synthesis of C-Glycosyl, (1987).
Bavin, M., "Process Development: Polymorphism in Process Development.", Chemistry & Industry, 1989, pp. 527-529, vol. 16.
Yamada, M., *Strategy and Novel Technology on Pharmaceutical Preparations*, CMC Publishing Co., Ltd., Mar. 31, 2007, First Copy, p. 152-171.
International Search Report relating to International Patent Application No. PCT/US2011/036038, filed May 11, 2011, dated Aug. 3, 2011.
Writtin Opinion of the International Searching Authority relating to International Patent Application No. PCT/US2011/036038, filed May 11, 2011, dated Aug. 3, 2011.
Notice of Opposition to European Patent/Opposition in corresponding EP application 11721616.8; issued as EP Patent 2568988, (Apr. 13, 2017).
Annex 1: Experimental Report, Apr. 12, 2017; (D10).
*A Textbook of Hospital and Clinical Pharmacology*, 28th edition, Paradkar, A.R. and Chunawala, S.A., Chapter 25, Bioavailability of Drugs, 1991, pp. 25.1, 25.3 and 25.4.
Brandsma et al., "Nickel- and Palladium-Catalyzed Cross-Coupling Reactions With Organometallic Intermediates.", *Application of Transition Metal Catalysts in Organic Synthesis*, 1999, Chapter 11, pp. 227-230, 243-246, 250-252, 258, 261, 273, Springer-Verlag Berlin Heidelberg, Germany.
Encyclopedia of Pharmaceutical Technology, Editors James Swarbrick and James C. Boylan; vol. 4, Design of Drugs to Drying and Driers; Marcel Dekker, Inc., 1991, cover pages and pp. 209-229 (D8).
Encyclopedia of Pharmaceutical Technology, Science Press, J. Swarbrick et al. editors, 2008, vol. 3, pp. 1821-1828 (A Chinese Textbook).
FMC Health and Nutrition, "Tablet Ingredients", Dr. Zak Chowhan, 1998, Section 4, pp. 1-8 (D5).
Kravovskiy et al., "A LiCl-Mediated Br/Mg—exchange reaction for produce functionalized aryl- and heteroarylymagnesium connections starting from organic bromides.", *Angew. Chem.*, 2004, pp. 3396-3399, vol. 116.
Kravovskiy et al., "Highly efficient reagents for the bromine-magnesium exchange.", *Angew. Chem.*, 2006, pp. 165-169, vol. 118.

(56) References Cited

OTHER PUBLICATIONS

Pharmacy, 6th edition, People's Publishing House, Cui Fude editor, 2008, pp. 127-128.
Remington, "The Science and Practice of Pharmacology", 21st Edition, Lippincott Williams & Wilkins, Editor: David Troy, 2006, Chapter 45, Cover pages and pp. 677-678 (D7).
Remington, "The Science and Practice of Pharmacology", 21st Edition, Lippincott Williams & Wilkins, Editor: David Troy, 2006, Chapter 45, Cover pages and pp. 891-892 (D6).
Ritschel et al., "Die Tablette" (The Pill), Handbuch der Entwicklung, Herstellung und Qualitatssicherung (Manual of development, production and quality assurance), 2. vollstandig Oberarbeitete und erweiterte Auflage, Ed. Cantor Verlag Aulendorf; 2002, pp. 64-65. (D9).
Schernthaner et al., "Erratum", *Diabetes Care*, Dec. 2013, p. 4172, vol. 36.
Takada, N., "Screening and selection of active pharmaceutical ingredient forms at the stage of drug development.", *Pharm Stage*, Jan. 15, 2007, vol. 6, No. 10, pp. 20-25.
The Extra Pharmaceutical Necessitits, Sichuan Publishing House of Science & Technology, Luo Mingsheng edit, 1993, vol. 3, pp. 73-79.
Tobyn et al., "Physicochemical comparison between microcrystalline cellulose and silicified microcrystalline cellulose.", International Journal of Pharmaceutics, Jul. 15, 1998, pp. 183-194, vol. 169 (2).
Veen et al., "Compaction Mechanism and tablet strength of unlubricated and lubricated (silicified) microcrystalline cellulose.", European Journal of Pharmaceutics and Biopharmaceuticals, 2005, pp. 133-138, vol. 59.
Wang, Wen-Ling et al., Chinese Journal of Clinical Pharmacology, 1992, vol. 8(1), pp. 25-31.
Yuan et al., "Pharmaceuticals Cocrystals.", Progress in Chemistry, May 2010, pp. 829-836, vol. 22(5).
Kipnes, M., "Dapagliflozin: an emerging treatment option in type 2 diabetes.", Expert Opinion Invest. Drugs, 2009, pp. 327-334, vol. 18(3).
Komoroski et al., "Dapagliflozin, a Novel SGLT2 Inhibitor, Induces Dose-Dependent Glucosuria in Healthy Subjects.", Nature, May 2009, pp. 520-526, vol. 85(5).
832133-18-0, Registry File, Mar. 4, 2005.
Brooks et al., "Dapagliflozin for the Treatment of Type 2 Diabetes.", The Annals of Pharmacotherapy, 2009, pp. 1286-1293, vol. 43.
EP opposition of EP 2568688, Appeal Number: T0323/19-3.3.01, Letter accompanying subsequently filed documents in LEK's appeal of decision of Jan. 25, 2019; Apr. 16, 2019.
Annex 1. Opponent's first data searchable. Apr. 12, 2017.
Comparison of dissolution profiles. May 16, 2019.
Dr. Bottjan Markun, Report: In vivo relevance of dissolution test. Aug. 9, 2018, pp. 1-9.
Amidon et al., "A Theoretical Basis for a Biopharmaceutic Drug Classification: The Correlation of in Vitro Drug Product Dissolution and in Vivo Bioavailability.", Pharm. Research, 1995, pp. 413-420, vol. 12(3).
Emami, J., "In vitro—In vivo Correlation: From Theory to Applications.", J. Pharm. Pharmaceut. Sci., 2006, pp. 31-51, vol. 9(2).
Annex 1, Summary of Product Characteristics., Aug. 10, 2018, pp. 1-39.
Note for Guidance on Quality of Modified Release Products: A: Oral Dosage Forms; B: Transdermal Dosage Forms; Section I (Quality)Committee for Proprietary Medicinal Products, the European Agency for the Evaluation of Medicinal Products Human Medicines Evaluation Unit, London, Uk, Jul. 29, 1999, pp. 1-16 (1/15 with title page).
Invokana web page information, downloaded Aug. 8, 2018, pp. 1-10.
Burjak, M. And Petek, B., Annex 1, Formulations, Aug. 9, 2018.
PCT Request, p. 5 of 6, relating to International patent application no. PCT/EP2011/054734, filed Mar. 28, 2011, published as WO/2011/120923, Oct. 6. 2011.
History of Changes for Study: NCT01106677, NIH, ClinicalTrials.gov archive, printed Jul. 23, 2018, 92 pages.
Hydroxypropyl Methylcellulose; Handbook of Pharmaceutical Excipients, Second Edition, edited by Ainley Wade and Paul J. Weller, 1994, pp. 229-232.
Joint Declaration of Christophe Tistaert and Anne Faure, Re. European Patent EP2568988B1; Oct. 2018, pp. 1-6.

\* cited by examiner

PHARMACEUTICAL FORMULATIONS

CROSS REFERENCE TO RELATED APPLICATIONS

This Application is a continuation application of U.S. application Ser. No. 14/486,014, filed Sep. 15, 2014, which is a continuation application of U.S. application Ser. No. 13/968,496, filed Aug. 16, 2013, abandoned, which is a continuation application of U.S. application Ser. No. 13/105,008, filed May 11, 2011, abandoned, which claims the benefit of U.S. Provisional Patent Application No. 61/333,495, filed May 11, 2010, the disclosures of which are hereby incorporated by reference herein in their entireties.

STATEMENT REGARDING FEDERALLY SPONSORED RESEARCH OR DEVELOPMENT

The research and development of the invention described below was not federally sponsored.

FIELD OF THE INVENTION

This invention relates to novel pharmaceutical compositions comprising a compound of Formula (I), a prodrug thereof, or a pharmaceutically acceptable salt thereof, disclosed herein, that can be used in the treatment of diabetes mellitus, obesity, diabetic complications, and related diseases.

BACKGROUND

WO 2005/012326, the disclosure of which is hereby incorporated by reference in its entirety, discloses a class of compounds that are inhibitors of sodium-dependent glucose transporter (SGLT) and therapeutic uses for such compounds such as the treatment of diabetes, obesity, diabetic complications, and the like. WO 2005/012326 discloses the compound 1-(β-D-glucopyranosyl)-4-methyl-3-[5-(4-fluorophenyl)-2-thienylmethyl]benzene). 1-(β-D-glucopyranosyl)-4-methyl-3-[5-(4-fluorophenyl)-2-thienylmethyl]benzene) hemihydrate and certain crystal form thereof are disclosed in WO 2008/069327, the disclosure of which is also hereby incorporated by reference in its entirety.

SUMMARY OF THE INVENTION

In its many embodiments, the present invention provides a novel pharmaceutical composition of compounds of Formula (I), a prodrug thereof, or a pharmaceutically acceptable salt thereof, and methods of treatment, prevention, inhibition or amelioration of one or more diseases associated with sodium-dependent glucose transporter using such pharmaceutical compositions.

One aspect of the present invention features an orally administrable pharmaceutical formulation comprising (a) compound of Formula (I)

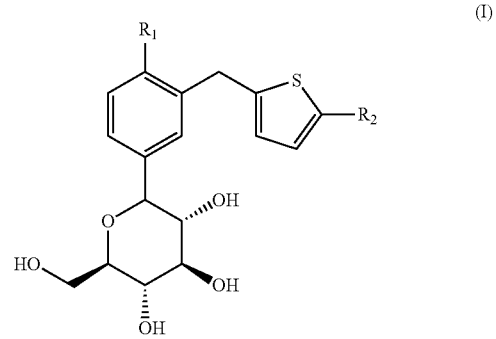

wherein
$R_1$ is halo, cyano, optionally substituted lower alkyl, or optionally substituted lower alkoxyl; and
$R_2$ is optionally substituted aryl, or optionally substituted heterocyclyl;
or a prodrug, or pharmaceutically acceptable salt thereof;
(b) at least one diluent or filler;
(c) optionally at least one disintegrant;
(d) optionally at least one binder; and
(e) optionally at least one lubricant;
wherein
the compound of formula (I) is present in an amount within the range of from about 1% to about 80% by weight;
the diluent or filler is present in an amount within the range of from about 10% to about 95% by weight;
the disintegrant, if present, is present in an amount within the range of from about 0.1% to about 20% by weight;
the binder, if present, is present in an amount within the range of from about 0.1% to about 20% by weight; and
the lubricant, if present, is present in an amount within the range of from about 0.1% to about 5% by weight, all of the above % by weight being based on the weight of the formulation.

In certain embodiments, the compound of Formula (I) is a compound of Formula (I-S) as described herein.

In certain embodiments, the present invention is directed to an orally administrable pharmaceutical formulation comprising a compound of Formula (I) as described herein in combination with a bioavailability-promoting agent.

In certain embodiments, the bioavailability-promoting agent increases the bioavailability of the compound and includes excipients known in the formulation of pharmaceuticals. Preferably formulating a compound of Formula (I) with the bioavailability-promoting agent results in improved measurable bioavailability of the compound upon administration of the formulation.

Preferably, the present invention is further directed to a bioavailability-promoting agent that includes a composition of excipients, such as binders, fillers, disintegrants, lubricants or combinations thereof.

In certain embodiments, the formulation of the present invention is a solid oral dosage form that provides for an increased bioavailability of the compound included therein as compared to an oral suspension including the compound in the same amount as the solid oral dosage form.

Additional embodiments and advantages of the invention will become apparent from the detailed discussion, schemes, examples, and claims below.

DETAILED DESCRIPTION OF THE INVENTION

Figure 1A:
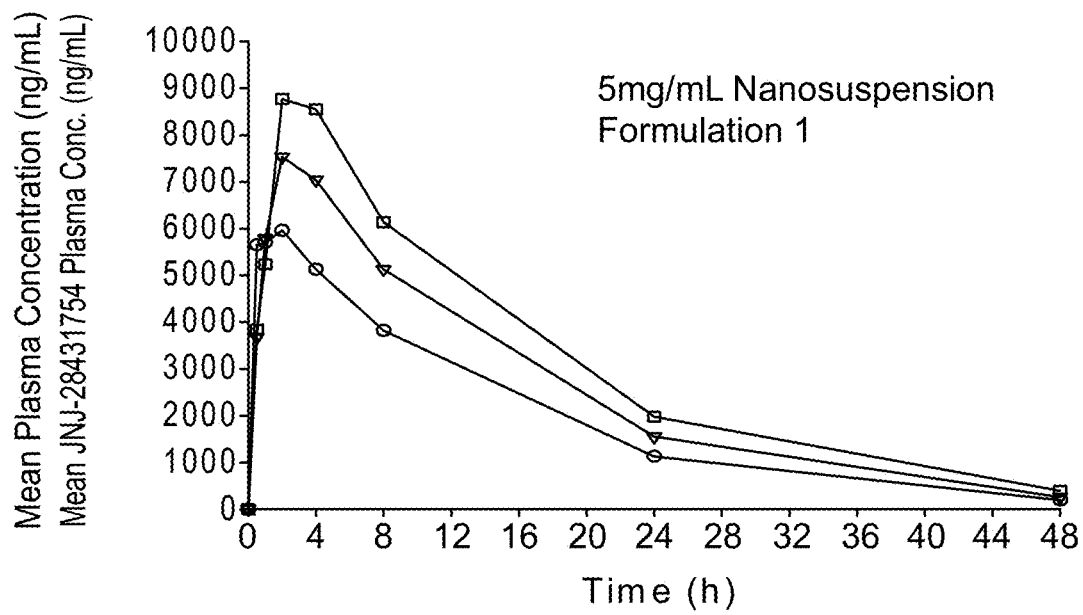
FIGS. 1A and B provides linear and logarithmic plasma concentration profiles of compound of Formula (I-S) following oral administration of various formulations of compound of Formula (I-S) in dogs.
Figure 1B:
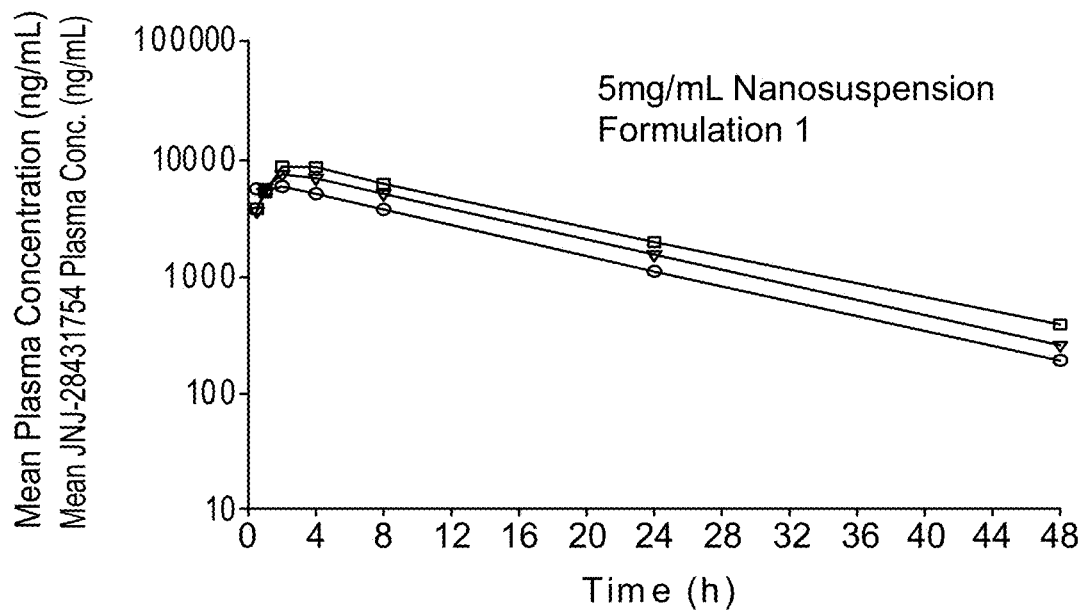

The present invention is directed in part to an orally administrable pharmaceutical formulation comprising
(a) a compound of Formula (I-S):

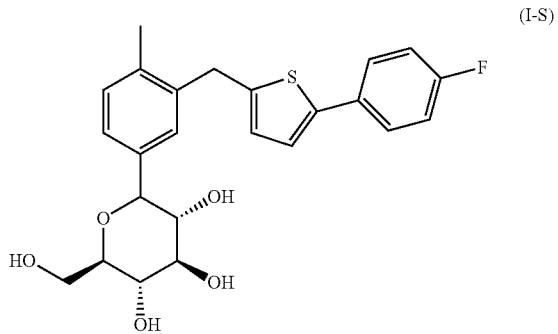 [SMILES: Cc1ccc(C2O[C@H](CO)[C@@H](O)[C@H](O)[C@H]2O)cc1Cc1ccc(-c2ccc(F)cc2)s1]

(I-S)

or a prodrug or pharmaceutically acceptable salt thereof;
(b) at least one diluent or filler;
(c) optionally at least one disintegrant;
(d) optionally at least one binder; and
(e) optionally at least one lubricant;
wherein
the compound of formula (I-S) is present in an amount within the range of from about 1% to about 80% by weight;
the diluent or filler is present in an amount within the range of from about 10% to about 95% by weight;
the disintegrant, if present, is present in an amount within the range of from about 0.1% to about 20% by weight;
the binder, if present, is present in an amount within the range of from about 0.1% to about 20% by weight; and
the lubricant, if present, is present in an amount within the range of from about 0.1% to about 5% by weight, all of the above % by weight being based on the weight of the formulation.

In certain embodiments, the present invention is directed to an orally administrable pharmaceutical formulation comprising
(a) a compound of Formula (I-S), or a prodrug or pharmaceutically acceptable salt thereof present in an amount within the range of from about 40% to about 60% by weight;
(b) at least one diluent or filler present in an amount within the range of from about 30% to about 50% by weight;
(c) at least one disintegrant in an amount within the range of from about 3% to about 10% by weight;
(d) at least one binder present in an amount within the range of from about 0.5% to about 5% by weight; and
(e) at least one lubricant present in an amount within the range of from about 0.5% to about 2% by weight;
wherein the % by weight is based on the weight of the formulation.

The compound of Formula (I-S) may also be referred to as 1-(β-D-glucopyranosyl)-4-methyl-3-[5-(4-fluorophenyl)-2-thienylmethyl]benzene).

In certain preferred embodiments, the compound of formula (I-S) is the hemihydrate of the compound of Formula (I-S), also referred to as 1-(β-D-glucopyranosyl)-4-methyl-3-[5-(4-fluorophenyl)-2-thienylmethyl]benzene) hemihydrate.

In certain embodiments, the invention is directed to a pharmaceutical composition as described herein for use in the manufacture of a pharmaceutical dosage form for oral administration to a mammal in need of treatment, characterized in that said dosage form can be administered at any time of the day independently of the food taken in by said mammal.

In certain embodiments, the invention is directed to a method of therapy of the human or non-human animal body that comprises administering to said body a therapeutically effective dose of a pharmaceutical composition described herein.

In certain embodiments, the invention is directed to a pharmaceutical package suitable for commercial sale comprising a container, an oral dosage form as described herein, and associated with said package written matter non-limited as to whether the dosage form can be administered with or without food.

A) Terms

Some terms are defined below and by their usage throughout this disclosure.

"Administering" or "administration" means providing a drug to a patient in a manner that is pharmacologically useful.

"Patient" or "subject" means an animal, preferably a mammal, more preferably a human, in need of therapeutic intervention.

"Dosage form" means one or more compounds in a medium, carrier, vehicle, or device suitable for administration to a patient. "Oral dosage form" means a dosage form suitable for oral administration.

"Dose" means a unit of drug. Conventionally, a dose is provided as a dosage form. Doses may be administered to patients according to a variety of dosing regimens. Common dosing regimens include once daily orally (qd), twice daily orally (bid), and thrice daily orally (tid).

"Terminal half-life" ($t_{1/2}$) is calculated as 0.693/k, wherein "k" means the apparent elimination rate constant, estimated by linear regression of the log-transformed plasma concentration during the terminal log-linear elimination phase. The plasma half-life of a drug ($t_{1/2}$) is the time necessary to halve the plasma concentration, for example to decrease from 100 to 50 mg/L. The knowledge of the half-life is useful for the determination of the frequency of administration of a drug (the number of intakes per day) for obtaining the desired plasma concentration. Generally, the half-life of a particular drug is independent of the dose administered. In certain exceptional cases, it varies with the dose: it can increase or decrease according to, for example, the saturation of a mechanism (elimination, catabolism, binding to plasma proteins etc).

"Area under the curve" or "AUC" is the area as measured under a plasma drug concentration curve, also termed plasma concentration profile. Often, the AUC is specified in terms of the time interval across which the plasma drug concentration curve is being integrated, for instance $AUC_{start\text{-}finish}$. Thus, $AUC_{0\text{-}48h}$ refers to the AUC obtained from integrating the plasma concentration curve over a period of zero to 48 hours, where zero is conventionally the time of administration of the drug or dosage form comprising the drug to a patient. $AUC_{int}$ refers to area under the plasma concentration curve from hour 0 to the last detectable concentration at time t, calculated by the trapezoidal rule. $AUC_{inf}$ refers to the AUC value extrapolated to infinity, calculated as the sum of $AUC_t$ and the area extrapolated to infinity, calculated by the concentration at time t $(C_t)$ divided by k. (If the $t_{1/2}$ value was not estimable for a subject, the mean $t_{1/2}$ value of that treatment was used to calculate $AUC_{inf}$).

"Mean area under a plasma concentration profile" means the mean $AUC_{inf}$ obtained over several patients or multiple administrations to the same patient on different occasions with sufficient washout in between dosings to allow drug levels to subside to pre-dose levels, etc., following a single administration of a dosage form to each patient.

"C" means the concentration of drug in blood plasma, or serum, of a subject, generally expressed as mass per unit volume, typically nanograms per milliliter. For convenience, this concentration may be referred to herein as "drug plasma concentration", "plasma drug concentration" or "plasma concentration". The plasma drug concentration at any time following drug administration is referenced as $C_{time}$, as in $C_{9h}$ or $C_{24h}$, etc. A maximum plasma concentration obtained following administration of a dosage form obtained directly from the experimental data without interpolation is referred to as $C_{max}$. The average or mean plasma concentration obtained during a period of interest is referred to as $C_{avg}$ or $C_{mean}$. "Mean, single dose, maximum plasma concentration $C_{max}$" means the mean $C_{max}$ obtained over several patients or multiple administrations to the same patient with sufficient washout in between dosing to allow drug levels to subside to pre-dose levels, etc., etc., following a single administration of a dosage form to each patient.

"Plasma concentration profile" refers to the curve obtained by plotting plasma concentration of the drug compound versus time. Usually, the convention is that the zero point on the time scale (conventionally on the x axis) is the time of administration of the drug compound or dosage form comprising the drug compound to a patient.

"Mean time to maximum plasma concentration" is the mean time elapsed from administration to a patient of a dosage form comprising a drug to the time at which the $C_{max}$ for that drug is obtained over several patients or multiple administrations to the same patient with sufficient washout in between dosing to allow drug levels to subside to pre-dose levels, etc., following a single administration of the dosage form to each patient, and obtained directly from the experimental data without interpolation.

The bioavailability indicates the percentage of the administered drug, which arrives in the central compartment. It is generally measured by comparing the AUC obtained after intravenous administration and after oral administration, for example. After intravenous administration, the AUC obtained corresponds to a bioavailability, which, by definition, is 100%; after oral administration, the AUC corresponds at best to an identical bioavailability. It is generally lower, sometimes null. In contrast, in this application bioavailability is indicated by the maximum plasma concentration $C_{max}$ reached after administration of the drug. A higher $C_{max}$ of a drug dosage form is indicative of better drug bioavailability via administrating this dosage form.

The compartment indicates the fictitious volume in which a drug would be distributed. It can correspond or not to a real volume, for example the volume of blood called first or central compartment, or the whole body except blood, called second compartment. The central compartment typically includes the plasma and in addition those tissues or parts in tissues in which drug concentrations rapidly come to equilibrium with the plasma. The real anatomical sectors in which the drug is distributed at different concentrations are represented by one, two, rarely three virtual compartments where the concentration of the drug is regarded as homogeneous. The concept of compartment thus makes it possible to model the fate of a drug.

The term "halo" means chlorine, bromine, iodine, and fluorine, and chlorine and fluorine are preferable.

The term "alkyl" or "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by one to five substituents as listed below, if necessary.

"Alkoxy" radicals are oxygen ethers formed from the previously described straight or branched chain alkyl groups. In some embodiments, the alkoxy may be optionally and independently be substituted with one to five, preferably one to three substituents defined below.

The term "alkylene group" or "alkylene group" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The substituent for the above each group includes, for example, a halogen atom (fluorine, chlorine, bromine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a hetero-cyclylcarbonyl group, an alkoxy-carbonyl group, an alkenyloxy-carbonyl group, an alkynyloxy-carbonyl group, a cycloalkyloxy-carbonyl group, a cycloalkenyl-oxy-carbonyl group, a cyclo-alkynyl-oxycarbonyl group, an aryloxycarbonyl group, a hetero-cyclyloxycarbonyl group, an alkanoyloxy group, an alkenyl-carbonyloxy group, an alkynyl-carbonyloxy group, a cycloalkyl-carbonyloxy group, a cycloalkenyl-carbonyloxy group, a cycloalkynyl-carbonyloxy group, an arylcarbonyloxy group, a hetero-cyclylcarbonyloxy group, an alkylthio group, an alkenyl-thio group, an alkynylthio group, a cycloalkylthio group, a cycloalkenyl-thio group, a cycloalkynylthio group, an arylthio group, a heterocyclyl-thio group, an amino group, a mono- or di-alkylamino group, a mono- or di-alkanoylamino group, a mono- or di-alkoxy-carbonyl-amino group, a mono- or di-arylcarbonyl-amino group, an alkylsulfinylamino group, an alkyl-sulfonyl-amino group, an arylsulfinylamino group, an aryl-sulfonylamino group, a carbamoyl group, a mono- or di-alkyl-carbamoyl group, a mono- or di-arylcarbamoyl group, an alkylsulfinyl group, an alkenyl-sulfinyl group, an alkynylsulfinyl group, a cycloalkyl-sulfinyl group, a cycloalkenylsulfinyl group, a cycloalkynyl-sulfinyl group, an arylsulfinyl group, a heterocyclyl-sulfinyl group, an alkyl-sulfonyl group, an alkenylsulfonyl group, an alkynyl-sulfonyl group, a cycloalkylsulfonyl group, a cycloalkenyl-sulfonyl group, a cycloalkynylsulfonyl group, an aryl-sulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylalkyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "composition" is intended to encompass a product comprising the specified ingredients in the specified amounts, as well as any product which results, directly or indirectly, from combinations of the specified ingredients in the specified amounts.

The term "prodrug" means an ester or carbonate, which is formed by reacting one or more hydroxy groups of the compound of the Formula (I) with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the Formula (I) with an α-amino acid or a β-amino acid, etc. using a condensing agent by a conventional method. In addition, the prodrug includes also ether, which is similarly formed by reacting one or more hydroxy groups of the compound of the Formula (I) with a condensing agent via a conventional method.

"Pharmaceutically acceptable" means molecular entities and compositions that are of sufficient purity and quality for use in the formulation of a composition or medicament of the present invention. Since both human use (clinical and over-the-counter) and veterinary use are equally included within the scope of the present invention, a formulation would include a composition or medicament for either human or veterinary use.

The term "pharmaceutically acceptable salt" refers includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of Formula (I) of the present invention also includes a mixture of stereoisomers, or each pure or substantially pure isomer. For example, the present compound may optionally have one or more asymmetric centers at a carbon atom containing any one of substituents. Therefore, the compound of the Formula (I) may exist in the form of enantiomer or diastereomer, or a mixture thereof. When the present compound of Formula (I) contains a double bond, the present compound may exist in the form of geometric isomerism (cis-compound, trans-compound), and when the present compound of Formula (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound of Formula (I) includes an intramolecular salt, hydrate, solvate or polymorphism thereof.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

B) Compounds

Compounds of Formula (I) exhibit an excellent inhibitory activity against sodium-dependent glucose transporter, and an excellent glucose lowering effect. Therefore, the formulation of the present invention is useful for treating or delaying the progression or onset of a sodium-dependent glucose transporter mediated disorder. In particular, the formulation of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the formulation of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

In certain preferred embodiments, $R_1$ as shown in Formula (I) is a halogen atom, or a lower alkyl group; and $R_2$ as shown in Formula (I) phenyl is optionally substituted by 1 to 3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group.

Preferably drug compounds of Formula (I) used in the disclosed formulation typically possess slight to poor water solubility in their crystalline or amorphous form and hence poor bioavailability, but the present invention is not necessarily limited to compounds with little to no water solubility.

Preferred representative compounds for use in the formulations of the present invention include 1-(β-D-glucopyranosyl)-4-methyl-3-[5-(4-fluorophenyl)-2-thienylmethyl]benzene), or a prodrug or a pharmaceutically acceptable salt thereof. In certain further preferred embodiments, the compound for use in the formulations of the present invention is 1-(β-D-glucopyranosyl)-4-methyl-3-[5-(4-fluorophenyl)-2-thienylmethyl]benzene) hemihydrate.

Preferably the 1-(β-D-glucopyranosyl)-4-methyl-3-[5-(4-fluorophenyl)-2-thienylmethyl]benzene), or a prodrug or a pharmaceutically acceptable salt thereof is included in the formulation of the present invention in an amount of from about 25 mg to about 600 mg, preferably from about 50 mg to about 400 mg.

In certain further preferred embodiments, the 1-(β-D-glucopyranosyl)-4-methyl-3-[5-(4-fluorophenyl)-2-thienylmethyl]benzene), or a prodrug or a pharmaceutically acceptable salt thereof is included in the formulation of the present invention in an amount of about 25 mg, about 50 mg, about 75 mg, about 100 mg, about 150 mg, about 200 mg, about 250 mg, about 300 mg, about 350 mg, or about 400 mg. In certain further preferred embodiments, the 1-(β-D-glucopyranosyl)-4-methyl-3-[5-(4-fluorophenyl)-2-thienylmethyl]benzene), or a prodrug or a pharmaceutically acceptable salt thereof is included in the formulation of the present invention in an amount of about 100 mg or about 300 mg. In certain embodiments, wherein the 1-(β-D-glucopyranosyl)-4-methyl-3-[5-(4-fluorophenyl)-2-thienylmethyl]benzene) is in the hemihydrate form the 1-(β-D-glucopyranosyl)-4-methyl-3-[5-(4-fluorophenyl)-2-thienylmethyl]benzene) hemihydrate is preferably included in the formulation in an amount of about 25.5 mg, about 51 mg, about 102 mg, about 204 mg, or about 306 mg, preferably in an amount of about 102 mg or about 306 mg.

C) Formulation

In embodiments of the present invention, the compound is formulated into oral dosage forms suitable for administration to patients in need thereof.

The oral dosage form may be provided in any pharmaceutically acceptable solid dosage form. Preferably, the solid dosage form includes, for example, solid preparation such as tablets, pills, granules, capsules, powders and others. More preferably, the solid dosage form is an oral tablet or capsule formulation. Most preferably the solid dosage form is an oral tablet.

In certain embodiments of the present invention the formulation includes a filler or diluent in the amount of about 10% to about 95% by weight of the formulation, preferably from about 25% to about 90% by weight of the formulation, more preferably from about 30% to about 50% by weight of the formulation or from about 35% to about 45% by weight of the formulation.

In certain embodiments of the present invention the formulation includes a disintegrant in the amount of about 0.1% to about 20% by weight of the formulation, preferably from about 0.25% to about 10% by weight of the formulation, more preferably from about 3% to about 10% by weight of the formulation or from about 5% to about 7% by weight of the formulation.

In certain embodiments of the present invention the formulation includes a binder in the amount of about 0.1% to about 20% by weight of the formulation, preferably from about 0.1% to about 10% by weight of the formulation, more preferably from about 0.5% to about 5% by weight of the formulation or from about 1% to about 4% by weight of the formulation.

In certain embodiments of the present invention the formulation includes a lubricant in the amount of about 0.1% to about 5% by weight of the formulation, preferably from about 0.1% to about 2% by weight of the formulation, more preferably from about 0.5% to 2% by weight of the formulation or 0.5% to 1.5% by weight of the formulation.

In certain embodiments of the present invention the formulation optionally includes a surfactant in the amount of about 0% to about 10% by weight of the formulation, preferably from about 0% to about 5% by weight of the formulation.

The solid dosage forms may comprise the compound in combination with various pharmaceutically acceptable excipients, and preferably the dosage form is adapted to provide increased bioavailability of the compound in a manner to obtain the desired clinical effect through oral administration to the patient.

The bioavailability promoting agent of the present invention includes any combination of the excipients described herein such that the formulation provides for the increase bioavailability of the compound included the formulation. In certain preferred embodiments, the bioavailability promoting agent includes two or more excipients described herein.

Pharmaceutically acceptable excipients are known in the art and can be provided according to considerations of desired functionality and process ability. Roles for the excipients in the oral dosage form include but are not limited to fillers, binders, disintegrants, release controlling agents, glidants, lubricants, coatings and the like.

For example, in one embodiment of the invention, it is desired to have an immediate release profile for the dosage form. To help achieve this profile in a solid dosage form, the dosage form preferably comprises a disintegrant in an amount as noted herein. In another embodiment of the invention, wherein a controlled or sustained release formulation of the compound is desired. Such a formulation can be achieved by varying the amounts, concentrations and ratios of certain release controlling polymers.

In one embodiment, the formulation of the present invention includes the compound in an amount of about 1% to about 80%, preferably from about 5% to about 60% by weight of the formulation, more preferably from about 40% to about 60% by weight of the formulation or about 45% to about 55% by weight of the formulation. Depending on the desired dose of the compound, one or more of the dosage forms can be administered.

For example, in one preferred embodiment of the invention, an oral release formulation is provided in tablet form comprising about 100 mg of 1-(β-D-glucopyranosyl)-4-methyl-3-[5-(4-fluorophenyl)-2-thienylmethyl]benzene), microcrystalline cellulose, hydroxypropyl cellulose, croscarmellose sodium, lactose anhydrous, and magnesium stearate.

In another preferred embodiment of the invention, an oral release formulation is provided in tablet form comprising about 300 mg of 1-(β-D-glucopyranosyl)-4-methyl-3-[5-(4-fluorophenyl)-2-thienylmethyl]benzene), microcrystalline cellulose, hydroxypropyl cellulose, croscarmellose sodium, lactose anhydrous, and magnesium stearate.

In another preferred embodiment of the invention, an oral release formulation is provided in tablet form comprising about 102 mg of 1-(β-D-glucopyranosyl)-4-methyl-3-[5-(4-fluorophenyl)-2-thienylmethyl]benzene) hemihydrate, microcrystalline cellulose, hydroxypropyl cellulose, croscarmellose sodium, lactose anhydrous, and magnesium stearate.

In another preferred embodiment of the invention, an oral release formulation is provided in tablet form comprising about 306 mg of 1-(β-D-glucopyranosyl)-4-methyl-3-[5-(4-fluorophenyl)-2-thienylmethyl]benzene) hemihydrate, microcrystalline cellulose, hydroxypropyl cellulose, croscarmellose sodium, lactose anhydrous, and magnesium stearate.

Fillers or diluents for use in the formulations of the present invention include fillers or diluents typically used in the formulation of pharmaceuticals. Examples of fillers or diluents for use in accordance with the present invention include but are not limited to sugars such as lactose, dextrose, glucose, sucrose, cellulose, starches and carbohydrate derivatives, polysaccharides (including dextrates and maltodextrin), polyols (including mannitol, xylitol, and sorbitol), cycludextrins, calcium carbonates, magnesium carbonates, microcrystalline cellulose, combinations thereof, and the like. In certain preferred embodiments the filler or diluent is lactose, microcrystalline cellulose, or combination thereof. Several types of microcrystalline cellulose are suitable for use in the formulations described herein, for example, microcrystalline cellulose selected from the group consisting of Avicel® types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate. In one embodiment of the invention, the filler or diluent is a combination of microcrystalline cellulose and lactose.

Binders for use in the formulations of the present invention include binders commonly used in the formulation of pharmaceuticals. Examples of binders for use in accordance with the present invention include but are not limited to cellulose derivatives (including hydroxypropyl cellulose, hydroxypropyl methylcellulose, methylcellulose, and sodium carboxymethyl cellulose), glycol, sucrose, dextrose, corn syrup, polysaccharides (including acacia, targacanth, guar, alginates and starch), corn starch, pregelatinized starch, modified corn starch, gelatin, polyvinylpyrrolidone, polyethylene, polyethylene glycol, combinations thereof and the like. Preferably, the binding agent, if present, is hydroxypropyl cellulose.

Disintegrants for use in the formulations of the present invention include disintegrants commonly used in the formulation of pharmaceuticals. Examples of disintegrants for use in accordance with the present invention include but are not limited to starches, clays, celluloses, alginates and gums and crosslinked starches, celluloses and polymers, combinations thereof and the like. Representative disintegrants include microcrystalline cellulose, croscarmellose sodium, alginic acid, sodium alginate, crosprovidone, cellulose, agar and related gums, sodium starch glycolate, corn starch, potato starch, sodiumstarch glycolate, Veegum HV, methylcellulose, agar, bentonite, carboxymethylcellulose, alginic acid, guar gum combinations thereof, and the like. Preferably, the disintegrant, if present, is a cross-linked cellulose, more preferably cross-linked sodium carboxymethylcellulose or croscarmellose sodium.

Lubricants for use in the formulations of the present invention include lubricants commonly used in the formulation of pharmaceuticals. Examples of lubricants for use in accordance with the present invention include but are not limited to magnesium carbonate, magnesium laurylsulphate, calcium silicate, talc, fumed silicon dioxide, combinations thereof, and the like. Other useful lubricants include but are not limited to magnesium stearate, calcium stearate, stearic acid, sodium stearyl fumarate, polyethylene glycol, sodium lauryl sulphate, magnesium lauryl sulphate, sodium benzoate, colloidal silicon dioxide, magnesium oxide, microcrystalline cellulose, starches, mineral oil, waxes, glyceryl behenate, polyethylene glycol, sodium acetate, sodium chloride, combinations thereof, and the like. Preferably, the lubricant, if present, is magnesium stearate or stearic acid, more preferably magnesium stearate.

Surfactants for use in the formulations of the present invention include surfactants commonly used in the formulation of pharmaceuticals. Examples of surfactants for use in accordance with the present invention include but are not limited to ionic- and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, combinations thereof, and the like.

Other polymers commonly used as excipients include but are not limited to methylcellulose (MC), ethylcellulose (EC), hydroxyethylcellulose (HEC), methyl hydroxyethylcellulose (MHEC), hydroxypropyl cellulose (HPC), hydroxypropyl methylcellulose (HPMC), sodium carboxymethylcellulose (NaCMC), and the like. These polymers, either alone or in various combinations, may serve multiple purposes including but not limited to controlling release of the compound of the formulations of the present invention.

In any case, the appropriate excipients should be selected such that they are compatible with other excipients and do not bind with the drug compound or cause drug degradation.

The pharmaceutical formulations disclosed herein can further comprise antioxidants and chelating agents. For example, the pharmaceutical formulations can comprise butylated hydroxyanisole (BHA), butylated hydroxytoluene (BHT), propyl gallate (PG), sodium metabisulfite, ascorbyl palmitate, potassium metabisulfite, disodium EDTA (ethylenediamine tetraacetic acid; also known as disodium edentate), EDTA, tartaric acid, citric acid, citric acid monohydrate, and sodium sulfite.

In another embodiment, the tablet or capsule of the invention has a protective outer layer. The protective outer layer of the tablet or capsule, where present, can include from about 10% to about 95% of polymer based on the weight of the coating layer, and can be prepared employing conventional procedures. In one embodiment, the outer layer of the tablet or capsule includes from about 20% to about 90% of polymer based on the weight of the coating layer. The formulation can contain at least one coating layer polymer and a coating solvent, for example, water, which is used for processing and removed by drying. Suitable examples of polymer for the coating layer include, but are not limited to, hydroxypropyl methylcellulose, polyvinyl alcohol (PVA), ethyl cellulose, methacrylic polymers, hydroxypropyl cellulose, and starch. In one embodiment, the coating layer polymer is PVA. In another embodiment, the coating layer polymer is hydroxypropyl cellulose.

The coating can also optionally include a plasticizer of from about 0% to about 30% by weight, based on the weight of the coating layer. In one embodiment, the plasticizer is from about 15% to about 25% by weight of the coating layer. Suitable plasticizers include, but are not limited to, triacetin, diethyl phthalate, tributyl sebacate, polyethylene glycol (PEG), glycerin, triacetin, and triaethyl citrate, for example.

In another embodiment, the coating can also optionally include an anti-adherent or glidant such as talc, fumed silica, or magnesium stearate, for example.

In another embodiment, the coating can also optionally include an opacifying agent, such as titanium dioxide, for example.

In yet another embodiment, wherein the formulation is a tablet, the tablet may be further coated with a coating layer that provides cosmetic benefits to the dosage form. In certain embodiments, such a coating helps to protect the tablets. In certain embodiments such coating comprises hydroxypropyl methylcellulose, polyethylene glycol, polydextrose, titanium dioxide, and triacetin. In certain other embodiments such coating comprises hydroxypropyl methylcellulose 2910, polyethylene glycol 400, polydextrose, titanium dioxide, carnuba wax, and iron oxide yellow. In at least one embodiment such a coating layer comprises Opadry® II (white) in an amount of from about 0% to about 10% by weight of the tablet; in certain other embodiments in an amount of from about 0% to about 6% by weight of the tablet; and in still other embodiments in an amount of from about, 0% to about 3% by weight of the tablet; and in other embodiments from about 2 to about 4% by weight of the tablet.

D) Additional Therapeutic Agents

In another embodiment the formulations of the present invention further include one or more additional therapeutic agents to provide the desired therapeutic effect.

Other therapeutic agent(s) suitable for combination with the formulations of the present invention include, but are not limited to, known therapeutic agents useful in the treatment of the aforementioned disorders associated with SGLT2 activity including: anti-diabetic agents; anti-hyperglycemic agents; hypolipidemic or lipid lowering agents; anti-obesity agents; anti-hypertensive agents and appetite suppressants.

The invention further provides a method for treating or delaying the progression or onset of diseases or disorders associated with SGLT2 activity comprising administering to a mammalian species in need of such treatment a therapeutically effective amount of the pharmaceutical formulation of the invention and one or more of the following: anti-diabetic agent(s), anti-hyperglycemic agent(s); hypolipidemic or lipid lowering agent(s); anti-obesity agent(s); anti-hypertensive agent(s) and appetite suppressant(s).

In one embodiment, the invention provides a method for treating type II diabetes comprising administering to a mammalian species in need of such treatment a therapeutically effective amount of the pharmaceutical formulation of the invention and one or more anti-diabetic agent(s). In another embodiment, the invention provides a method for delaying the progression or onset of type II diabetes comprising administering to a mammalian species in need of such treatment a therapeutically effective amount of the pharmaceutical formulation of the invention and one or more anti-diabetic agent(s).

In another embodiment, the invention provides a method for treating or delaying the progression or onset of type II diabetes comprising administering to a mammalian species in need of such treatment a therapeutically effective amount of the pharmaceutical formulation of the invention and one or more of the following: anti-hyperglycemic agent(s); hypolipidemic or lipid lowering agent(s); anti-obesity agent (s); anti-hypertensive agent(s) and appetite suppressant(s). For example, the invention provides a method for treating or delaying the progression or onset of type II diabetes comprising administering to a mammalian species in need of such treatment a therapeutically effective amount of a pharmaceutical formulation of the invention and an anti-hyperglycemic agent(s). In another embodiment, the invention provides a method for treating or delaying the progression or onset of type II diabetes comprising administering to a mammalian species in need of such treatment a therapeutically effective amount of a pharmaceutical formulation of the invention and a hypolipidemic agent(s). In another embodiment, the invention provides a method for treating or delaying the progression or onset of type II diabetes comprising administering to a mammalian species in need of such treatment a therapeutically effective amount of a pharmaceutical formulation of the invention and an anti-obesity agent(s). In another embodiment, the invention provides a method for treating or delaying the progression or onset of type II diabetes comprising administering to a mammalian species in need of such treatment a therapeutically effective amount of a pharmaceutical formulation of the invention and an anti-hypertensive agent(s). In another embodiment, the invention provides a method for treating or delaying the progression or onset of type II diabetes comprising administering to a mammalian species in need of such treatment a therapeutically effective amount of a pharmaceutical formulation of the invention and an appetite suppressant(s).

Examples of suitable anti-diabetic agents for use in combination with the formulations of the present invention include, but are not limited to, biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) and other agonists of the GLP-1 receptor, and dipeptidyl peptidase IV (DPP4) inhibitors.

Other suitable thiazolidinediones include, but are not limited to, MCC-555, faraglitazar, englitazone or darglitazone; isaglitazone, reglitazar, rivoglitazone, liraglutide, and (Z)-1,4-bis-4-[(3,5-dioxo-1,2,4-oxadiazolidin-2-yl-methyl)] phenoxybut-2-ene.

Examples of PPAR-alpha agonists, PPAR-gamma agonists and PPAR alpha/gamma dual agonists include, but are not limited to, muraglitazar, peliglitazar, tesaglitazar AR-H039242, GW-501516, and IRP297.

Suitable DPP4 inhibitors include, but are not limited to, sitigliptin and saxagliptin.

Examples of suitable anti-hyperglycemic agents for use in combination with the formulations of the present invention include, but are not limited to, glucagon-like peptide-1 (GLP-1) such as GLP-1 (1-36) amide, GLP-1 (7-36) amide, GLP-1 (7-37), exenatide, LY-315902, MK-0431, liraglutide, ZP-10, and CJC-1131.

Examples of suitable hypolipidemic/lipid lowering agents for use in combination with the formulations of the present invention include one or more MTP inhibitors, HMG CoA reductase inhibitors (such as e.g., mevastatin, lovastatin, pravastatin, simvastatin, fluvastatin, cerivastatin, atorvastatin, atavastatin, rosuvastatin), squalene synthetase inhibitors, fibric acid derivatives (such as e.g., fenofibrate, gemfibrozil, clofibrate, bezafibrate, ciprofibrate, clinofibrate and the like, probucol, bile acid sequestrants, such as cholestyramine, colestipol and DEAE-Sephadex, as well as lipostabil), ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as torcetrapib and JTT-705, PPAR agonists (as described above) and/or nicotinic acid and derivatives thereof. Preferred hypolipidemic agents include pravastatin, lovastatin, simvastatin, atorvastatin, fluvastatin, cerivastatin, atavastatin and rosuvastatin, for example.

Examples of suitable anti-hypertensive agents for use in combination with the formulations of the present invention include, but are not limited to, beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), and ET receptor antagonists (e.g., sitaxsentan, and atrsentan). Examples of suitable anti-obesity agents for use in combination with the formulations of the present invention include, but are not limited to, beta 3 adrenergic agonists, lipase inhibitors, serotonin (and dopamine) reuptake inhibitors, thyroid receptor beta drugs, 5HT2C agonists; MCHR1 antagonists, such as Synaptic SNAP-7941 and Takeda T-226926, melanocortin receptor (MC4R) agonists, melanin-concentrating hormone receptor (MCHR) antagonists, galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, ciliary neurotrophic factors, BDNF (brain-derived neurotrophic factor), leptin and leptin receptor modulators, cannabinoid-1 receptor antagonists, and anorectic agents.

Examples of lipase inhibitors that can be employed in combination with formulations of the present invention include, but are not limited to, orlistat and ATL-962 (Alizyme).

Serotonin (and dopamine) reuptake inhibitors (or serotonin receptor agonists) that can be employed in combination with the formulations of the present invention include, but are not limited to, BVT-933, sibutramine, topiramate and axokine.

Examples of monoamine reuptake inhibitors that can be employed in combination with the formulations of the present invention include, but are not limited to, fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Anorectic agents that can be employed in combination with the formulations of the present invention include, but are not limited to, topiramate, dexamphetamine, phentermine, phenylpropanolamine and mazindol.

Where any of the formulations of the invention are used in combination with other therapeutic agent(s), the other therapeutic agent(s) can be used, for example, in the amounts indicated in the Physician's Desk Reference, or as otherwise known and used by one of ordinary skill in the art.

Where any of the formulations of the invention are used in combination with other therapeutic agent(s), each of the compounds of the combination can be administered simultaneously or sequentially and in any order, and the components can be administered separately or as a fixed combination, in jointly therapeutically effective amounts, for example, in daily dosages as described herein. In one embodiment of the invention, a fixed combination of the invention can be prepared by mixing a dry granulation of the compound of Formula (I) or (I-S) or formulation of the invention and a dry granulation of the other therapeutic agent(s) and filling the mixture into capsules of desired size, shape, color, or other characteristics, or compressing to form tablets.

E) Manufacturing of Formulation

In certain embodiments, the formulations of the invention are prepared by making an admixture of the drug compound, and a bioavailability-promoting agent. Dissolving these components in a liquid solvent therefore and subsequently removing the solvent may affect this most straightforwardly. Thus viewed from a further aspect the invention provides a process for the preparation of a pharmaceutical composition, said process comprising: dissolving a drug compound, and the pharmaceutically acceptable excipients in a solvent; removing solvent from the resultant solution; optionally forming the resultant product into desired shapes; and optionally coating the resulting product with a physiologically tolerable coating material.

Preferably, dosage forms in accordance with the embodiments depicted herein are manufactured by standard techniques. For example, the dosage form may be manufactured by the wet granulation technique. In the wet granulation technique, the drug and carrier are blended using an aqueous or organic solvent, such as denatured anhydrous ethanol, as the granulation fluid. The remaining ingredients can be dissolved in a portion of the granulation fluid, such as the solvent described above, and this latter prepared wet blend is slowly added to the drug blend with continual mixing in the blender. The granulating fluid is added until a wet blend is produced, which wet mass blend is then forced through a predetermined screen and dried in a fluid bed dryer. The dried granules are then sized. Next, magnesium stearate, or another suitable lubricant and other excipient materials are added to the drug granulation, and the granulation is put into milling jar sand mixed on a jar mill for 10 minutes. The composition is pressed into a layer, for example, in a Manesty® press or a Korsch LCT press. For a trilayered core, granules or powders of the drug layer compositions and push layer composition are sequentially placed in an appropriately-sized die with intermediate compression steps being applied to each of the first two layers, followed by a final compression step after the last layer is added to the die to form the trilayered core. The intermediate compression typically takes place under a force of about 50-100 Newtons. Final stage compression typically takes place at a force of 3500 Newtons or greater, often 3500-5000 Newtons. The compressed cores are fed to a dry coater press, e.g., Kilian® Dry Coaterpress, and subsequently coated with the wall materials as described herein.

Pan coating may be conveniently used to provide the completed dosage form. In the pan coating system, the wall-forming composition for the inner wall or the outer wall, as the case may be, is deposited by successive spraying of the appropriate wall composition onto the compressed core accompanied by tumbling in a rotating pan. A pan coater is used because of its availability at commercial scale. Other techniques can be used for coating the compressed core. Once coated, the wall is dried in a forced-air oven or in a temperature and humidity controlled oven to free the dosage form of solvent(s) used in the manufacturing. Drying conditions will be conventionally chosen on the basis of available equipment, ambient conditions, solvents, coatings, coating thickness, and the like.

Other coating techniques can also be employed. For example, one alternative technique uses an air-suspension procedure. This procedure consists of suspending and tumbling the compressed core in a current of air, until a coating is applied to the core. The air-suspension procedure is described in U.S. Pat. No. 2,799,241; in J. Am. Pharm. Assoc., Vol. 48, pp. 451-459 (1959); and, ibid., Vol. 49, pp. 82-84 (1960). The dosage form also can be coated with a Wurster® air-suspension coater using, for example, methylene dichloride methanol as a cosolvent for the wall forming material. An Aeromatic® air-suspension coater can be used employing a cosolvent.

In another embodiment, the drug and other ingredients comprising the drug layer are blended and pressed into a solid layer. The layer possesses dimensions that correspond to the internal dimensions of the area the layer is to occupy in the dosage form, and it also possesses dimensions corresponding to the push layer, if included, for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. The compressed cores then may be coated with the inner wall material and the semipermeable wall material as described herein.

Another manufacturing process that can be used comprises blending the powdered ingredients in a fluid bed granulator. After the powdered ingredients are dry blended in the granulator, a granulating fluid, for example, polyvinylpyrrolidone in water, is sprayed onto the powders. The coated powders are then dried in the granulator. This process granulates all the ingredients present therein while adding the granulating fluid. After the granules are dried, a lubricant, such as stearic acid or magnesium stearate, is mixed into the granulation using a blender e.g., V-blender or tote blender. The granules are then pressed and coated in the manner described above.

Exemplary solvents suitable for manufacturing the dosage form components comprise aqueous or inert organic solvents that do not adversely harm the materials used in the system. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethylacetate, isopropyl acetate, n-butyl acetate, methyl isobutyl ketone, methyl propyl ketone, nhexane, n-heptane, ethylene glycol monoethyl ether, ethylene glycol monoethyl acetate, methylene dichloride, ethylene dichloride, propylene dichloride, carbon tetrachloridenitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

Exemplary liquid carriers for the present invention include lipophilic solvents (e.g., oils and lipids), surfactants, and hydrophilic solvents. Exemplary lipophilic solvents, for example, include, but are not limited to, Capmul PG-8, Caprol MPGO, Capryol 90, Plurol Oleique CC497, Capmul MCM, Labrafac PG, N-Decyl Alcohol, Caprol 10G100, Oleic Acid, Vitamin E, Maisine 35-1, Gelucire 33/01, Gelucire 44/14, Lauryl Alcohol, Captex 355EP, Captex 500, Capylic/Caplic Triglyceride, Peceol, Caprol ET, Labrafil M2125 CS, Labrafac CC, Labrafil M20 1944 CS, Captex 8277, Myvacet 9-45, Isopropyl Nyristate, Caprol PGE 860, Olive Oil, Plurol Oleique, Peanut Oil, Captex 300 Low C6, and Capric Acid.

Exemplary surfactants for example, include, but are not limited to, Vitamin E TPGS, Cremophor (grades EL, EL-P, and RH40), Labrasol, Tween (grades 20, 60, 80), Pluronic (gradesL-31, L-35, L-42, L-64, and L-121), Acconon S-35, Solutol HS-15, and Span (grades 20, and 80).

Exemplary hydrophilic solvents for example, include, but are not limited to, Isosorbide Dimethyl Ether, Polyethylene Glycol (PEG grades 300, 400, 600, 3000, 4000, 6000, and 8000) and Propylene Glycol (PG).

In general, essentially complete solvent removal will be preferred as the resultant product can then readily be shaped. Shaping may be effected by spray-drying the solution (to provide the product in particulate form), by evaporation of solvent from solution disposed in molds, by molding (e.g. injection molding), by extrusion and the like. In general the product can be formed when hot and allowed to solidify on cooling. The shaped product may likewise be produced in film or sheet form by evaporation or by pouring a heated mass onto a plate and evaporating off the solvent.

F) Formulation Examples

The following formulation examples are illustrative only and are not intended to limit the scope of the inventions in any way. Tablets were prepared using the ingredients listed in Tables 1.1-1.6 and the following procedure.

In the following examples in Table 1.1-1.6, the exemplified compound, lactose anhydrous, microcrystalline cellulose, and croscarmellose sodium were screened and placed into a fluid bed.

Hydroxypropyl cellulose and purified water were mixed to prepare the granulating solution.

The granulating solution was sprayed into the fluid bed to granulate the dry ingredients.

When the granulating solution was exhausted, the granulation was dried within the fluid bed.

The dried granules were passed through a suitable mill fitted with an appropriate screen.

The milled granulation was placed in an appropriate blender and combined with screened magnesium stearate.

The mixture was blended for an appropriate period of time.

A suitable rotary tablet press was employed to compress the final blend into tablets.

Where a filmcoating was utilized (e.g., Opadry II), the filmcoating powder was mixed with purified water to obtain the film-coating suspension.

The tablets were filmcoated in a suitable coating pan and dried.

TABLE 1.1

100 mg Tablet Formulation

| Ingredient | Weight (mg/tablet) | % Weight/tablet |
|---|---|---|
| 1-(β-D-glucopyranosyl)-4-methyl-3-[5-(4-fluorophenyl)-2-thienylmethyl]benzene) hemihydrate[1] | 102.00 | 51.00% |
| Silicified Microcystralline Cellulose | 39.26 | 19.63% |
| Lactose Anhydrous | 39.26 | 19.63% |
| Hydroxypropyl Cellulose | 6.00 | 3.00% |
| Croscarmellose Sodium | 12.00 | 6.00% |
| Magnesium Stearate | 1.48 | 0.74% |
| Total | 200.00 | 100% |

[1]amount of hemihydrate equivalent to 100 mg of 1-(β-D-glucopyranosyl)-4-methyl-3-[5-(4-fluorophenyl)-2-thienylmethyl]benzene)

TABLE 1.2

25 mg Tablet Formulation

| Ingredient | Weight (mg/tablet) | % Weight/tablet |
|---|---|---|
| 1-(β-D-glucopyranosyl)-4-methyl-3-[5-(4-fluorophenyl)-2-thienylmethyl]benzene) hemihydrate[1] | 25.50 | 12.75% |
| Silicified Microcystralline Cellulose | 81.76 | 40.88% |
| Lactose Anhydrous | 81.76 | 40.88% |
| Hydroxypropyl Cellulose | 1.50 | 0.75% |
| Croscarmellose Sodium | 8.00 | 4.00% |
| Magnesium Stearate | 1.48 | 0.74% |
| Total | 200.00 | 100% |

[1]amount of hemihydrate equivalent to 25 mg of 1-(β-D-glucopyranosyl)-4-methyl-3-[5-(4-fluorophenyl)-2-thienylmethyl]benzene)

TABLE 1.3

200 mg Tablet Formulation

| Ingredient | Weight (mg/tablet) | % Weight/tablet |
|---|---|---|
| 1-(β-D-glucopyranosyl)-4-methyl-3-[5-(4-fluorophenyl)-2- | 204.00 | 51.00% |

TABLE 1.3-continued

200 mg Tablet Formulation

| Ingredient | Weight (mg/tablet) | % Weight/tablet |
|---|---|---|
| thienylmethyl]benzene) hemihydrate[1] | | |
| Silicified Microcystralline Cellulose | 78.52 | 19.63% |
| Lactose Anhydrous | 78.52 | 19.63% |
| Hydroxypropyl Cellulose | 12.00 | 3.00% |
| Croscarmellose Sodium | 24.00 | 6.00% |
| Magnesium Stearate | 2.96 | 0.74% |
| Total | 400.00 | 100% |

[1]amount of hemihydrate equivalent to 200 mg of 1-(β-D-glucopyranosyl)-4-methyl-3-[5-(4-fluorophenyl)-2-thienylmethyl]benzene)

TABLE 1.4

50 mg Tablet Formulation

| Ingredient | Weight (mg/tablet) | % Weight/tablet |
|---|---|---|
| 1-(β-D-glucopyranosyl)-4-methyl-3-[5-(4-fluorophenyl)-2-thienylmethyl]benzene) hemihydrate[1] | 51.00 | 51.00% |
| Silicified Microcystralline Cellulose | 19.63 | 19.63% |
| Lactose Anhydrous | 19.63 | 19.63% |
| Hydroxypropyl Cellulose | 3.00 | 3.00% |
| Croscarmellose Sodium | 6.00 | 6.00% |
| Magnesium Stearate | 0.74 | 0.74% |
| Total | 100.00 | 100% |

[1]amount of hemihydrate equivalent to 50 mg of 1-(β-D-glucopyranosyl)-4-methyl-3-[5-(4-fluorophenyl)-2-thienylmethyl]benzene)

TABLE 1.5

300 mg coated Tablet Formulation

| Ingredient | Weight (mg/tablet) | % Weight/tablet |
|---|---|---|
| 1-(β-D-glucopyranosyl)-4-methyl-3-[5-(4-fluorophenyl)-2-thienylmethyl]benzene) hemihydrate[1] | 306.00 | 51.50% |
| Microcystralline Cellulose | 117.78 | 19.63% |
| Lactose Anhydrous | 117.78 | 19.63% |
| Hydroxypropyl Cellulose | 18.00 | 3.00% |
| Croscarmellose Sodium | 36.00 | 6.00% |
| Magnesium Stearate | 4.44 | 0.74% |
| Total | 600.00 | 100% |
| Opadry II[2] | 18.00 | 3.00% |

[1]amount of hemihydrate equivalent to 300 mg of 1-(β-D-glucopyranosyl)-4-methyl-3-[5-(4-fluorophenyl)-2-thienylmethyl]benzene)
[2]Tablets are coated to a 3% weight gain with Opadry II

TABLE 1.6

100 mg coated Tablet Formulation

| Ingredient | Weight (mg/tablet) | % Weight/tablet |
|---|---|---|
| 1-(β-D-glucopyranosyl)-4-methyl-3-[5-(4-fluorophenyl)-2-thienylmethyl]benzene) hemihydrate[1] | 102.00 | 51.00% |
| Microcystralline Cellulose | 39.26 | 19.63% |
| Lactose Anhydrous | 39.26 | 19.63% |
| Hydroxypropyl Cellulose | 6.00 | 3.00% |
| Croscarmellose Sodium | 12.00 | 6.00% |
| Magnesium Stearate | 1.48 | 0.74% |
| Total | 200.00 | 100% |
| Opadry II[2] | 8.00 | 4.00% |

[1]amount of hemihydrate equivalent to 100 mg of 1-(β-D-glucopyranosyl)-4-methyl-3-[5-(4-fluorophenyl)-2-thienylmethyl]benzene)
[2]Tablets are coated to a 4% weight gain with Opadry II G) Biological Examples In Vivo Pharmacokinetic Data from Dog Studies Exposure of 1-(β-D-glucopyranosyl)-4-methyl-3-[5-(4-fluorophenyl)-2-thienylmethyl]benzene) in dogs was compared using various orally administrable formulations. Eleven male beagle dogs weighing from 8.0 to 10.0 kg at dose administration and exhibiting good general health were chosen for this study. The dogs were placed into 3 groups according to their weight. Following an overnight fast each dog received either a single oral suspension dosage or tablet dosage form. In total, three dosage forms of drug compound 1-(β-D-glucopyranosyl)-4-methyl-3-[5-(4-fluorophenyl)-2-thienylmethyl]benzene) were administered: a 5 mg/mL nanosuspension, the 100 mg Tablet Formulation and 25 mg Tablet Formulation. Three fasted dogs in Group 1 received 20 mL of a 5 mg/mL nanosuspension; 4 fasted dogs assigned to Group 2 received the 100 mg Tablet Formulation (1 tablet per dog; ingredients listed in Table 1.1); and the 4 fasted dogs assigned to Group 3 received the 25 mg Tablet Formulation (4 tablets per dog; ingredients listed in Table 1.2).

Following each dose, the dogs received 10 mL of tap water to ensure delivery of the entire dose. Blood samples of about 3 mL were collected via jugular venipuncture, or other suitable site, into $K_2$ EDTA tubes and placed on wet ice, at times of 0, 0.5, 1, 2, 4, 8, 24, and 48 hours post initial dosing. Plasma was harvested by centrifugation, and frozen at −20° C. All samples were placed in amber vials for protection from white light and were processed within two hours of collection.

Plasma samples were analyzed for plasma concentrations of drug compound 1-(β-D-glucopyranosyl)-4-methyl-3-[5-(4-fluorophenyl)-2-thienylmethyl]benzene) by using a liquid chromatographic-triple quadruple mass spectrometric (LC-MS/MS) assay procedure with a lower limit of quantification of 50 ng/mL. Plasma concentration data were electronically transferred to a Watson™ LIMS computer system. The Watson™ system assigns a value of 0.00 to those concentrations below the lower limit of quantification.

TABLE 2

| Dosage/Formulation | Subject ID | Body Weight (kg) | $C_{max}$ (ng/mL) | $t_{max}$ (h) | $AUC_{0-48h}$ (ng · h/mL) | $AUC_{inf}$ (ng · h/mL) | $t_{1/2}$ (h) | CL/F (mL/h) |
|---|---|---|---|---|---|---|---|---|
| 20 mL of 5 mg/mL nanosuspension | 1 | 9.10 | 6480 | 2.00 | 114000 | 119000 | 10.4 | 763 |
| | 2 | 8.10 | 7760 | 0.500 | 105000 | 107000 | 8.01 | 759 |
| | 3 | 9.90 | 4210 | 1.00 | 64300 | 66000 | 9.24 | 1500 |

TABLE 2-continued

| Dosage/Formulation | Subject ID | Body Weight (kg) | $C_{max}$ (ng/mL) | $t_{max}$ (h) | $AUC_{0-48h}$ (ng · h/mL) | $AUC_{inf}$ (ng · h/mL) | $t_{1/2}$ (h) | CL/F (mL/h) |
|---|---|---|---|---|---|---|---|---|
| | Mean | 9.03 | 6150 | 1.17 | 94600 | 97300 | 9.23 | 1008 |
| | SD | 0.902 | 1800 | 0.764 | 26700 | 27900 | 1.22 | 427 |
| 1 × 100 mg tablet | 4 | 10.0 | 9670 | 2.00 | 147000 | 153000 | 10.5 | 656 |
| | 5 | 8.00 | 6440 | 2.00 | 95800 | 97300 | 7.95 | 1030 |
| | 6 | 8.30 | 7910 | 1.00 | 116000 | 118000 | 8.49 | 847 |
| | 7 | 9.80 | 7230 | 4.00 | 137000 | 142000 | 9.63 | 705 |
| | Mean | 9.03 | 7810 | 2.25 | 124000 | 127000 | 9.13 | 809 |
| | SD | 1.02 | 1380 | 1.26 | 22700 | 24700 | 1.13 | 167 |
| 4 × 25 mg tablets | 8 | 8.60 | 11100 | 4.00 | 180000 | 188000 | 10.8 | 532 |
| | 9 | 9.30 | 9640 | 4.00 | 155000 | 161000 | 9.83 | 621 |
| | 10 | 8.30 | 7460 | 4.00 | 157000 | 163000 | 10.4 | 612 |
| | 11 | 8.80 | 9360 | 2.00 | 109000 | 112000 | 8.86 | 895 |
| | Mean | 8.75 | 9390 | 3.50 | 150000 | 156000 | 9.97 | 665 |
| | SD | 0.420 | 1500 | 1.00 | 29600 | 32000 | 0.845 | 159 |

The nanosuspension used as a control in the study included a 0.5% Methocel® suspension measured in weight percentage. Methocel® is a hydroxypropyl methylcellulose (HPMC) polymer exhibiting high viscosity and used as a thickener of the suspension. The drug concentration was 5 mg of drug per 1 mL of suspension volume. A total of 20 mL suspension was administered to each dog in the nanosuspension group.

Pharmacokinetic analysis of the plasma concentrations of drug compound 1-(β-D-glucopyranosyl)-4-methyl-3-[5-(4-fluorophenyl)-2-thienylmethyl]benzene) was performed to determine the maximum plasma concentration ($C_{max}$), the time to maximum plasma concentration ($t_{max}$), the area under the plasma concentration versus time curve extrapolated to infinity ($AUC_{inf}$ and $AUC_{0-48h}$), the terminal half-life ($t_{1/2}$), and the plasma clearance (CL/F) using the WinNonlin Version 4.0.1 (Pharsight) validated computer program.

Furthermore, bioavailability, as indicated by $AUC_{inf}$, following administration of the compound of the 100 mg Tablet Formulation or the 25 mg Tablet Formulation was higher than after the administration of the 5 mg/mL nanosuspension.

In Vivo Pharmacokinetic Data from Human Studies

Healthy human subjects received single oral doses of a liquid nanosuspension or tablet formulation under fed and/or fasted conditions at three different dose levels of the drug compound 1-(β-D-glucopyranosyl)-4-methyl-3-[5-(4-fluorophenyl)-2-thienylmethyl]benzene). The three dose levels included 25 mg (representative formulation listed in Table 1.2), 200 mg (representative formulation listed in Table 1.3) and 400 mg of the drug compound. In particular, the 400 mg tablet dose was achieved by administering two doses of the 200 mg Tablet Formulation.

The mean plasma concentration profiles of the compound following oral administration of the 200 mg Tablet Formu-

TABLE 3

| Formulation | | Body Weight (kg) | $C_{max}$ (ng/mL) | $t_{max}$ (h) | $t_{1/2}$ (h) | $AUC_{0-48h}$ (ng · h/mL) | $AUC_{inf}$ (ng · h/mL) | Bioavailability | CL/F (mL/h) |
|---|---|---|---|---|---|---|---|---|---|
| 20 mL of 5 mg/mL | Mean | 9.03 | 6150 | 1.17 | 9.23 | 94600 | 97300 | Reference | 1008 |
| nanosuspension | SD | (0.902) | (1800) | (0.764) | (1.22) | (26700) | (27900) | | (427) |
| 1 × 100 mg Tablet | Mean | 9.03 | 7810 | 2.25 | 9.13 | 124000 | 127000 | 127 | 809 |
| | SD | (1.020) | (1380) | (1.26) | (1.13) | (22700) | (24700) | | (167) |
| 4 × 25 mg Tablet | Mean | 8.75 | 9390 | 3.50 | 9.97 | 150000 | 156000 | 153 | 665 |
| | SD | (0.420) | (1500) | (1.00) | (0.845) | (29600) | (32000) | | (159) |

Following a single 20 mL oral dose of a 5 mg/mL nanosuspension of the compound to male beagle dogs, absorption of the compound was rapid based on a mean $t_{max}$ value of 1.17 hours and its elimination was slow based on a mean $t_{1/2}$ value of 9.23 hours. Administration of the single oral dose of 100 mg Tablet Formulation or four doses of the 25 mg Tablet Formulation of the compound showed delayed absorption of the compound as indicated by mean $t_{max}$ values of 2.25 and 3.50 hours, respectively.

Figure 2:
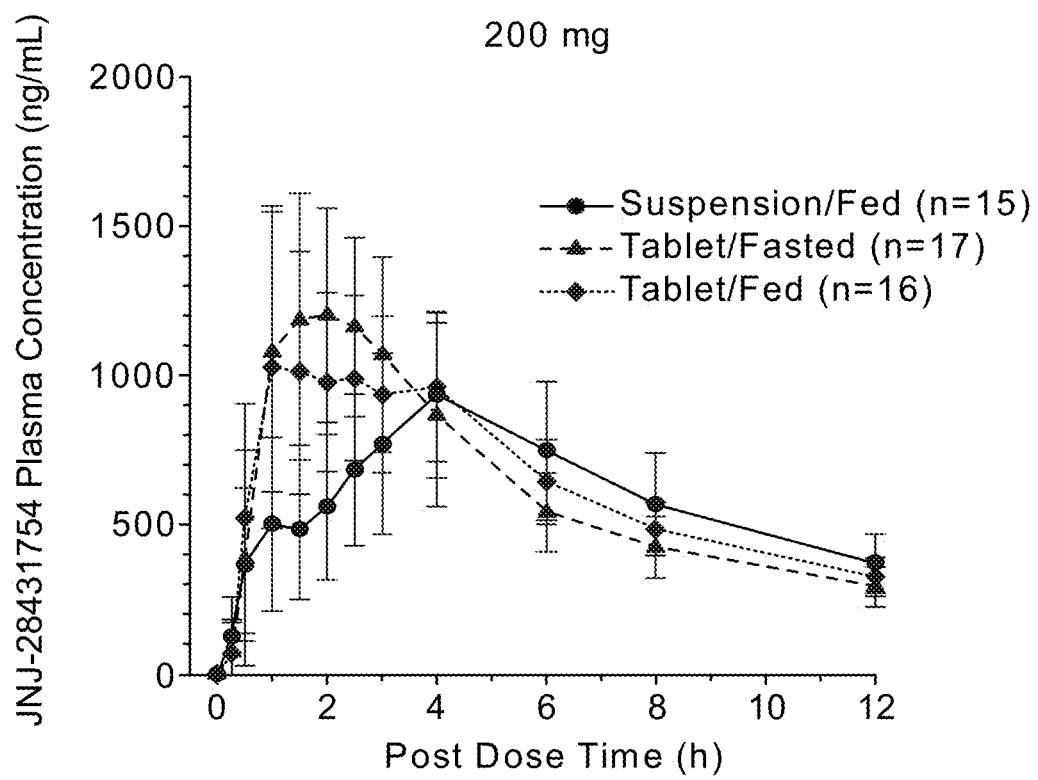
FIG. 2 provides plasma concentration profiles of compound (I-S) following oral administration of various formulations of compound of Formula (I-S) in human subjects.

Yet, the elimination of the compound after administration of both Tablet Formulations remained slow with mean $t_{1/2}$ values 9.13 and 9.97 hours, respectively. Based on mean plasma pharmacokinetic parameters that were normalized to 1 mg/kg, the maximum plasma concentration ($C_{max}$) of the compound following oral administration of one dose of the 100 mg Tablet Formulation and four doses of the 25 mg Tablet Formulation was higher as compared to the 5 mg/mL nanosuspension (FIGS. 1A & B).

lation under fasted and fed condition and 40 mL of the 5 mg/mL liquid nanosuspension (fed condition) are shown in FIG. 2. Similar profiles for the Tablet Formulation versus the nanosuspension were obtained at doses of 25 mg and 400 mg.

Following 25 and 200 mg doses under fed conditions as shown in Table 4, the median time to maximum plasma concentration ($t_{max}$) of the compound was approximately 1 to 1.5 hours for Tablet Formulations versus 4 hours in case of the nanosuspension. At the 400 mg dose level, median $t_{max}$ was approximately 1.75 hours for 2 doses of the 200 mg Tablet Formulation versus 2.25 hours in case of the nanosuspension.

For all doses (25 mg, 200 mg, 400 mg), under fed conditions, the mean $C_{max}$ was lower for the nanosuspension formulation compared to the Tablet Formulations.

Following administration of 25 and 200 mg doses of the Tablet Formulation, the mean $C_{max}$ was higher under fasted conditions than under fed conditions. For all doses (25 mg, 200 mg and 400 mg), under fed or fasting (25 mg and 200 mg Tablet Formulation only) conditions, mean $AUC_{inf}$ values of the compound were comparable.

TABLE 4

|  | Nanosuspension | Tablet | Tablet |
|---|---|---|---|
|  | 25 mg Dose | | |
| Food Intake | Fed | Fasted | Fed |
| Number of subjects | 17 | 17 | 18 |
| $C_{max}$ (ng/mL) | 130.6 (38.6) | 217.1 (52.0) | 183.9 (46.1) |
| $t_{max}^a$ (hr) | 4.0 (1-6) | 1.5 (1-4) | 1.0 (1-3) |
| $t_{1/2}$ (hr) | 7.9 (1.6) | 8.1 (1.9) | 7.6 (1.2) |
| $AUC_{inf}$ (ng × h/mL) | 1,476 (368) | 1,441 (347) | 1,462 (421) |
| Bioavailability | Reference | 166.2 | 140.8 |
|  | 200 mg Dose | | |
| Food Intake | Fed | Fasted | Fed |
| Number of subjects | 15 | 17 | 16 |
| $C_{max}$ (ng/mL) | 985.9 (273.4) | 1,411.7 (319.8) | 1,284.3 (320.5) |
| $t_{max}^a$ (hr) | 4.0 (3-6) | 1.5 (1-3) | 1.5 (1-4) |
| $t_{1/2}$ (hr) | 12.4 (4.2) | 12.1 (2.4) | 11.9 (2.6) |
| $AUC_{inf}$ (ng × h/mL) | 13,007 (2881) | 12,291 (2579) | 12,846 (2489) |
| Bioavailability | Reference | 143.2 | 130.3 |
|  | 400 mg Dose | | |
| Food Intake | Fed | 30 Min. Prior to Breakfast | With Breakfast |
| Number of subjects | 12 | 12 | 12 |
| $C_{max}$ (ng/mL) | 1,683.3 (310.1) | 2,412.5 (727.6) | 2,315.0 (474.9) |
| $t_{max}^a$ (hr) | 2.25 (0.5-6) | 1.5 (1-4) | 1.75 (1-2.5) |
| $t_{1/2}$ (hr) | 11.8 (3.7) | 11.0 (3.9) | 10.1 (4.0) |
| $AUC_{inf}$ (ng × h/mL) | 24,520 (4599) | 26,158 (11263) | 23,667 (2259) |
| Bioavailability | Reference | 143.3 | 137.5 |

$^a$Data represents mean (SD) values

These data suggest that food had no significant effect on the extent of bioavailability to the drug compound, but it decreased the rate of absorption as evidenced by a decrease in $C_{max}$ and delay in $t_{max}$.

Following tablet administration at the 400 mg dose (2×200 mg tablets), altering meal-timing (dosing 30 minutes prior to breakfast versus dosing 10 minutes prior to breakfast) did not appear to influence $t_{max}$, $t_{1/2}$, $C_{max}$, or $AUC_\infty$.

For all treatment regimens regardless of formulation and food intake, the mean $t_{1/2}$ of the drug compound ranged from about 8 to about 12 h.

We claim:

1. An orally administrable pharmaceutical tablet comprising
   (a) a compound which is 1-(β-D-glucopyranosyl)-4-methyl-3-[5-(4-fluorophenyl)-2-thienylmethyl]benzene), or a prodrug or pharmaceutically acceptable salt thereof present in an amount within a range of from about 1% to about 80% by weight;
   (b) a diluent or filler consisting of a combination of microcrystalline cellulose and lactose, wherein the diluent or filler is present in an amount within a range of from about 10% to about 95% by weight;
   (c) croscarmellose sodium in an amount within a range of from about 0.1 to about 20% by weight;
   (d) hydroxypropyl cellulose in an amount within a range of from about 0.1 to about 20% by weight; and
   (e) magnesium stearate in an amount within a range of from about 0.1% to about 5% by weight;
   wherein the % by weight is based on a weight of the tablet.

2. The pharmaceutical tablet of claim 1, wherein the compound of (a) is 1-(β-D-glucopyranosyl)-4-methyl-3-[5-(4-fluorophenyl)-2-thienylmethyl]benzene) hemihydrate.

3. The pharmaceutical tablet of claim 1, wherein the compound of (a) is present in an amount of about 25 mg to about 600 mg.

4. The pharmaceutical tablet of claim 1, wherein the compound of (a) is present in an amount of about 50 mg to about 300 mg.

5. The pharmaceutical tablet of claim 1, wherein the compound of (a) is present in an amount of about 100 mg.

6. The pharmaceutical tablet of claim 1, wherein the compound of (a) is present in an amount of about 300 mg.

7. A method for treating a sodium-dependent glucose transporter mediated disorder, said method comprising administering to a patient in need thereof, the pharmaceutical tablet of claim 1.

8. The method of claim 7 wherein the compound of (a) is administered at a dose of from about 50 mg to about 300 mg once daily.

9. The method of claim 7 wherein the compound of (a) is administered at a dose of about 100 mg per day.

10. The method of claim 7 wherein the compound of (a) is administered at a dose of about 300 mg per day.

* * * * *